(12) United States Patent
Tomura et al.

(10) Patent No.: US 6,895,800 B2
(45) Date of Patent: May 24, 2005

(54) GAS CONCENTRATION MEASURING APPARATUS MINIMIZING MEASUREMENT ERROR

(75) Inventors: Takanao Tomura, Nishio (JP); Michiyasu Moritsugu, Okazaki (JP); Eiichi Kurokawa, Okazaki (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 83 days.

(21) Appl. No.: 10/328,147

(22) Filed: Dec. 26, 2002

(65) Prior Publication Data

US 2003/0121311 A1 Jul. 3, 2003

(30) Foreign Application Priority Data

Dec. 27, 2001 (JP) .......................................... 2001-397360
Nov. 5, 2002 (JP) .......................................... 2002-321044

(51) Int. Cl.[7] ............................ G01N 7/00; G01N 27/26
(52) U.S. Cl. .................... 73/23.31; 73/23.32; 73/31.05; 204/425; 204/426; 204/427
(58) Field of Search .............................. 73/23.31, 23.32, 73/31.05, 35.05; 204/424, 425, 426, 427

(56) References Cited

U.S. PATENT DOCUMENTS 5,866,799 A  2/1999  Kato et al. ................. 73/31.05
6,231,735 B1 *  5/2001  Poggio et al. ............... 204/425
6,295,862 B1  10/2001  Kurokawa et al. ......... 73/31.05
6,656,337 B2 * 12/2003  Kurokawa et al. .......... 204/425

FOREIGN PATENT DOCUMENTS

EP        0798555 A2    10/1997
JP        9-318596      12/1997
JP        2885336       2/1999
JP        2000-137018   5/2000

* cited by examiner

*Primary Examiner*—Daniel S. Larkin
(74) *Attorney, Agent, or Firm*—Nixon & Vanderhye P.C.

(57) ABSTRACT

A gas concentration measuring apparatus has a gas sensor including pump, sensor, and monitor cells. The apparatus works to look up a predetermined voltage-to-current relation to determine an initial value to be applied to the pump cell as a function of a current output of the pump cell, apply the initial value of the voltage to the pump cell, and to sweep it temporarily. The apparatus works to correct the initial value of the voltage as a function of a current output of the sensor cell upon the sweep of the initial value of the voltage applied to the pump cell, thereby better maintaining gas concentration measuring accuracy with respect to, for example, aging of the sensor.

15 Claims, 15 Drawing Sheets

GAS CONCENTRATION MEASURING APPARATUS MINIMIZING MEASUREMENT ERROR

BACKGROUND OF THE INVENTION

1. Technical Field of the Invention

The present invention relates generally to a gas concentration measuring apparatus for measuring the concentration of a gas which may be employed in an air-fuel ratio control system for automotive vehicles, and more particularly to a such a gas concentration measuring apparatus designed to minimize error in determining the concentration of a gas.

2. Background Art

Limiting current type gas concentration sensors are known which are used for measuring NOx contained in exhaust gasses of an automotive engine. One such gas concentration sensor includes a pump cell and a sensor cell which are made of solid electrolyte bodies. The pump cell works to pump oxygen ($O_2$) contained in gasses admitted into a gas chamber out of the sensor and to pump oxygen ($O_2$) of outside gasses into the gas chamber selectively. The sensor cell works to measure the concentration of NOx contained in the gasses after passing through the pump cell. The pump cell and the sensor cell are designed to produce current signals indicative of the concentration of oxygen and NOx upon application of voltage thereto.

Another type of gas concentration sensor is known which includes a monitor cell in addition to the pump cell and the sensor cell. The monitor cell works to produce an electromotive force as a function of the concentration of oxygen within the gas chamber. A control system is also proposed which controls the voltage to be applied to the pump cell of such a three-cell gas concentration sensor as a function of a difference between an actual value and a target value of the electromotive force of the monitor cell.

For example, Japanese Patent No. 2885336 discloses the above type of gas concentration sensor.

The above discussed gas concentration sensors, however, have a drawback in that unit-to-unit variation and/or aging of the sensors usually results in a change in resistance or impedance of a solid electrolyte body, thereby leading to a decrease in accuracy of determining the concentration of a gas.

SUMMARY OF THE INVENTION

It is therefore a principal object of the present invention to avoid the disadvantages of the prior art.

It is another object of the present invention to provide a gas concentration measuring apparatus designed to eliminate an error in determining the concentration of a specified gas component of measurement gases arising from a unit-to-unit variation and/or aging of a gas concentration sensor.

According to one aspect of the invention, there is provided a gas concentration measuring apparatus which may be employed with an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber; (b) a pump cell-applied voltage determining circuit looking up a predetermined voltage-to-current relation to determine an initial value of the voltage to be applied to the pump cell as a function of the pump cell current produced by the pump cell; and (c) a pump cell-applied voltage correcting circuit working to apply the initial value of the voltage to the pump cell and sweep the initial value to at least one of higher and lower level sides The pump cell-applied voltage correcting circuit corrects the initial value of the voltage applied to the pump cell as a function of a magnitude of the monitor cell current produced by the monitor cell upon a sweep of the initial value of the voltage applied to the pump cell.

The voltage applied to the pump cell (will also be labeled Vp below) and the monitor cell current (will also be labeled Im below) have a relation in which the monitor cell current changes at a greater rate within a range of lower levels of the pump cell-applied voltage and remains unchanged substantially within a range of higher levels of the pump cell-applied voltage (see a Vp-Im curve in FIG. 2(b)). Specifically, the pump cell applied voltage-to-monitor cell current relation has an inflection point at which the rate of a change in monitor cell current changes greatly. The relation between the pump cell-applied voltage and the sensor cell current (will also be referred to as a sensor cell current Is below) has a flat range in which the sensor cell current hardly changes regardless of a change in the pump cell-applied voltage. Within the flat range, it is possible to measure the concentration of a gas component such as NOx contained in exhaust gasses of automotive engines accurately (see a Vp-Is curve in FIG. 2(b)). The aging and/or a unit-to-unit variation of the gas concentration sensor usually results in changes in the pump cell applied voltage-to-monitor cell current relation and the pump cell applied voltage-to-sensor cell current relation, thereby causing the inflection point of the pump cell applied voltage-to-monitor cell current relation to move close to or away from an initial value of the pump cell-applied voltage. The location of the inflection point may, therefore, be determined by sweeping the pump cell-applied voltage temporarily to measure the magnitude of a change in the monitor cell current. Production of the sensor cell current within the flat range may be accomplished by correcting the initial value of the pump cell-applied voltage as a function of the change in the monitor cell current, thereby keeping the accuracy of measuring the concentration of the gas free from the unit-to-unit variation and/or aging of the gas concentration sensor.

In the preferred mode of the invention, the pump cell-applied voltage correcting circuit works to determine a difference between a value of the voltage applied to the pump cell appearing at an inflection point of a pump cell applied voltage-to-monitor cell current curve indicative of a relation between the voltage applied to the pump cell and a resulting value of the monitor cell current produced by the monitor cell and the initial value of the voltage applied to the pump cell based on the value of the monitor cell current produced upon the sweep of the voltage applied to the pump cell. The inflection point is defined by a level of the voltage applied to the pump cell at which the rate of a change in the monitor cell current changes over a given value. The pump cell-applied voltage correcting circuit corrects the initial value of the voltage applied to the pump cell based on the determined difference.

The pump cell-applied voltage correcting circuit may sweep the initial value of the voltage only to one of the higher and lower level sides.

The pump cell-applied voltage correcting circuit may alternatively sweep the initial value of the voltage both to the higher and lower level sides. This specifies a locational relation between the initial value of the pump cell-applied voltage and the inflection point of the pump cell applied voltage-to-monitor cell current curve.

The pump cell-applied voltage correcting circuit may sweep the initial value of the voltage both to the higher and lower level sides sequentially to measure resulting changes in the monitor cell current, respectively. The pump cell-applied voltage correcting circuit compares the changes with each other to determine whether the initial value of the voltage applied to the pump cell should be corrected or not as a function of a difference between the changes. In a case where the pump cell-applied voltage is set within the flat range of the monitor cell current and far from the inflection point, the changes in monitor cell current arising from the sweep of the pump cell-applied voltage both to the positive and negative sides are substantially identical with each other. If this is one of original sensor characteristics of the gas concentration sensor, the pump cell-applied voltage correcting circuit decides (a) that the pump cell-applied voltage needs not be corrected when changes in monitor cell current arising from the sweep of the pump cell-applied voltage to the positive side and to the negative side are substantially identical with each other and (b) that the pump cell-applied voltage should be corrected when changes in monitor cell current Im differs from each other.

When the pump cell-applied voltage correcting circuit sweeps the initial value of the voltage both to the higher and lower level sides sequentially to measure resulting changes in the monitor cell current, respectively, and when the changes are different from those appearing initially at the gas concentration sensor and from each other, the pump cell-applied voltage correcting circuit may shift the initial value of the voltage applied to the pump cell to a direction opposite a direction in which the monitor cell current increases with a change in the voltage applied to the pump cell.

The correction of the pump cell-applied voltage is made for eliminating effects of the unit-to-unit variation and/or aging of the gas concentration sensor on the accuracy of measuring the concentration of the gas and preferably reflects on a subsequent gas measuring operation. It is, thus, advisable that the pump cell-applied voltage correcting circuit determine a voltage correction value used in correcting the initial value of the voltage applied to the pump cell as a function of the monitor cell current upon the sweep of the initial value of the voltage applied to the pump cell and store the voltage correction value in a backup memory. The pump cell-applied voltage correcting circuit may alternatively correct the predetermined voltage-to-current relation.

The pump cell-applied voltage correcting circuit may control the voltage applied to the pump cell so as to bring a value of the monitor cell current produced upon the sweep of the initial value of the voltage applied to the pump cell to within a given controlled range.

When the value of the monitor cell current produced upon the sweep of the initial value of the voltage applied to the pump cell lies out of the given controlled range, the pump cell-applied voltage correcting circuit may increase or decrease the voltage applied to the pump cell.

The pump cell-applied voltage correcting circuit may sweep the initial value of the voltage at different amplitudes sequentially to measure resulting changes in the monitor cell current and correct the initial value of the voltage applied to the pump cell based on the changes in the monitor cell current.

The gas concentration measuring apparatus may further comprise a deterioration determining circuit which works to determine a degree of deterioration of the gas concentration sensor based on the magnitude of the monitor cell current produced by the monitor cell upon the sweep of the initial value of the voltage applied to the pump cell. The pump cell-applied voltage determining circuit determines the initial value of the voltage to be applied to the pump cell as a function of the pump cell current produced by the pump cell by look-up using the predetermined voltage-to-current relation for determining the concentration of the specified gas component in a gas concentration measuring cycle. The pump cell-applied voltage correcting circuit works to correct the initial value of the voltage applied to the pump cell in a correction cycle which uncoincides with the gas concentration measuring cycle.

When the pump cell-applied voltage correcting circuit sweeps the initial value of the voltage applied to the pump cell, resulting values of the monitor cell current and the sensor cell current may be filtered to blur waveforms thereof.

The gas concentration sensor may work to measure the specified gas component contained in exhaust gasses of an automotive engines, and wherein the pump cell-applied voltage correcting circuit operates at at least one of startup and rest of the engine.

According to the second aspect of the invention, there is provided a gas concentration measuring apparatus which comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber; (b) a pump cell-applied voltage determining circuit looking up a predetermined voltage-to-current relation to determine an initial value of the voltage to be applied to the pump cell as a function of the pump cell current produced by the pump cell; and (c) a deterioration determining circuit working to apply the initial value of the voltage to the pump cell and sweep the initial value temporarily. The deterioration determining circuit determines a degree of deterioration of the gas concentration sensor based on a magnitude of the monitor cell current produced by the monitor cell upon the sweep of the initial value of the voltage applied to the pump cell.

The aging and/or a unit-to-unit variation of the gas concentration sensor usually results in an increase in resistance or impedance of the gas concentration sensor. Control of the pump cell-applied voltage, thus, encounters a difficulty in discharging a desired quantity of oxygen from gas chamber. This results in a shift in inflection point of a pump cell applied voltage-to-monitor cell current curve indicative of a relation between the voltage applied to the pump cell and a resulting value of the monitor cell current produced by the monitor cell and the initial value of the voltage applied to the pump cell. The determination of deterioration of the gas concentration sensor may, therefore, be made based on the magnitude of the monitor cell current produced by the monitor cell upon the sweep of the initial value of the voltage applied to the pump cell.

In the preferred mode of the invention, the gas concentration sensor may work to measure the specified gas component contained in exhaust gasses of an automotive engines, and wherein the deterioration determining circuit operates at at least one of startup and rest of the engine.

According to the third aspect of the invention, there is provided a gas concentration measuring apparatus which comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber; (b) a pump cell-applied voltage determining circuit looking up a predetermined voltage-to-current relation to determine an initial value of the voltage to be applied to the pump cell as a function of the pump cell current produced by the pump cell; and (c) a pump cell-applied voltage correcting circuit working to apply the initial value of the voltage to the pump cell and sweep the initial value to at least one of higher and lower level sides. The pump cell-applied voltage correcting circuit corrects the initial value of the voltage applied to the pump cell as a function of a magnitude of the sensor cell current produced by the sensor cell upon a sweep of the initial value of the voltage applied to the pump cell.

The pump cell-applied voltage and the sensor cell current have a relation in which the sensor cell current changes at a greater rate within a range of lower levels of the pump cell-applied voltage and remains unchanged substantially within a range of higher levels of the pump cell-applied voltage (see a Vp-Is curve in FIG. 2(b)). Specifically, the pump cell applied voltage-to-sensor cell current relation has an inflection point at which the rate of a change in sensor cell current changes greatly. The relation also has a flat range in which the sensor cell current hardly changes regardless of a change in the pump cell-applied voltage. Therefore, the pump cell-applied voltage correcting circuit, as described above, corrects the initial value of the voltage applied to the pump cell as a function of a magnitude of the sensor cell current produced by the sensor cell upon the sweep of the initial value of the voltage applied to the pump cell.

The aging and/or a unit-to-unit variation of the gas concentration sensor usually results in changes in the pump cell applied voltage-to-monitor cell current and the pump cell applied voltage-to-sensor cell current, thereby causing the inflection point of the pump cell applied voltage-to-sensor cell current relation to move close to or away from an initial value of the pump cell-applied voltage. The location of the inflection point may, therefore, be determined by sweeping the pump cell-applied voltage temporarily to measure the magnitude of a change in the sensor cell current. Production of the sensor cell current within the flat range may be accomplished by correcting the initial value of the pump cell-applied voltage as a function of the change in the sensor cell current, thereby keeping the accuracy of measuring the concentration of the gas free from the unit-to-unit variation and/or aging of the gas concentration sensor.

In the preferred mode of the invention, the pump cell-applied voltage correcting circuit works to determine a difference between a value of the voltage applied to the pump cell appearing at an inflection point of a pump cell applied voltage-to-sensor cell current curve indicative of a relation between the voltage applied to the pump cell and a resulting value of the sensor cell current produced by the sensor cell and the initial value of the voltage applied to the pump cell based on the value of the sensor cell current produced upon the sweep of the voltage applied to the pump cell. The inflection point is defined by a level of the voltage applied to the pump cell at which a rate of a change in the sensor cell current changes over a given value. The pump cell-applied voltage correcting circuit corrects the initial value of the voltage applied to the pump cell based on the determined difference.

The pump cell-applied voltage correcting circuit may sweep the initial value of the voltage only to one of the higher and lower level sides. The pump cell-applied voltage correcting circuit may alternatively sweep the initial value both to the higher and lower level sides.

The pump cell-applied voltage correcting circuit may sweep the initial value of the voltage both to the higher and lower level sides sequentially to measure resulting changes in the sensor cell current, respectively and compare the changes with each other to determine whether the initial value of the voltage applied to the pump cell should be corrected or not as a function of a difference between the changes.

When the pump cell-applied voltage correcting circuit sweeps the initial value of the voltage both to the higher and lower level sides sequentially to measure resulting changes in the sensor cell current, respectively, and when the changes are different from those appearing initially at the gas concentration sensor and from each other, the pump cell-applied voltage correcting circuit shifts the initial value of the voltage applied to the pump cell to a direction opposite a direction in which the sensor cell current increases with a change in the voltage applied to the pump cell.

The pump cell-applied voltage correcting circuit may determine a voltage correction value used in correcting the initial value of the voltage applied to the pump cell as a function of the sensor cell current upon the sweep of the initial value of the voltage applied to the pump cell and stores the voltage correction value in a backup memory.

The pump cell-applied voltage correcting circuit may alternatively correct the predetermined voltage-to-current relation using the voltage correction value.

The pump cell-applied voltage correcting circuit may control the voltage applied to the pump cell so as to bring a value of the sensor cell current produced upon the sweep of the initial value of the voltage applied to the pump cell to within a given controlled range.

When the value of the sensor cell current produced upon the sweep of the initial value of the voltage applied to the pump cell lies outside of the given controlled range, the pump cell-applied voltage correcting circuit may increase or decrease the voltage applied to the pump cell.

The pump cell-applied voltage correcting circuit may sweep the initial value of the voltage at different amplitudes sequentially to measure resulting changes in the sensor cell current and corrects the initial value of the voltage applied to the pump cell based on the changes in the sensor cell current.

The gas concentration measuring apparatus may further comprise a deterioration determining circuit which works to determine a degree of deterioration of the gas concentration sensor based on the magnitude of the sensor cell current produced by the monitor cell upon the sweep of the initial value of the voltage applied to the pump cell.

The pump cell-applied voltage determining circuit may determine the initial value of the voltage to be applied to the pump cell as a function of the pump cell current produced by the pump cell by look-up using the predetermined voltage-to-current relation for determining the concentration of the specified gas component in a gas concentration measuring cycle. The pump cell-applied voltage correcting circuit may work to correct the initial value of the voltage applied to the pump cell in a correction cycle which does not coincide with the gas concentration measuring cycle.

When the pump cell-applied voltage correcting circuit sweeps the initial value of the voltage applied to the pump cell, resulting values of the monitor cell current and the sensor cell current may be filtered to blur waveforms thereof.

The gas concentration sensor may work to measure the specified gas component contained in exhaust gasses of an automotive engines, and wherein the pump cell-applied voltage correcting circuit operates at at least one of startup and rest of the engine.

According to the fourth aspect of the invention, there is provided a gas concentration measuring apparatus which comprises: (a) a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber; (b) a pump cell-applied voltage determining circuit looking up a predetermined voltage-to-current relation to determine an initial value of the voltage to be applied to the pump cell as a function of the pump cell current produced by the pump cell; and (c) a deterioration determining circuit working to apply the initial value of the voltage to the pump cell and sweep the initial value temporarily. The deterioration determining circuit determines a degree of deterioration of the gas concentration sensor based on a magnitude of the sensor cell current produced by the monitor cell upon the sweep of the initial value of the voltage applied to the pump cell.

The gas concentration sensor may work to measure the specified gas component contained in exhaust gasses of an automotive engines, and wherein the deterioration determining circuit operates at at least one of startup and rest of the engine.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
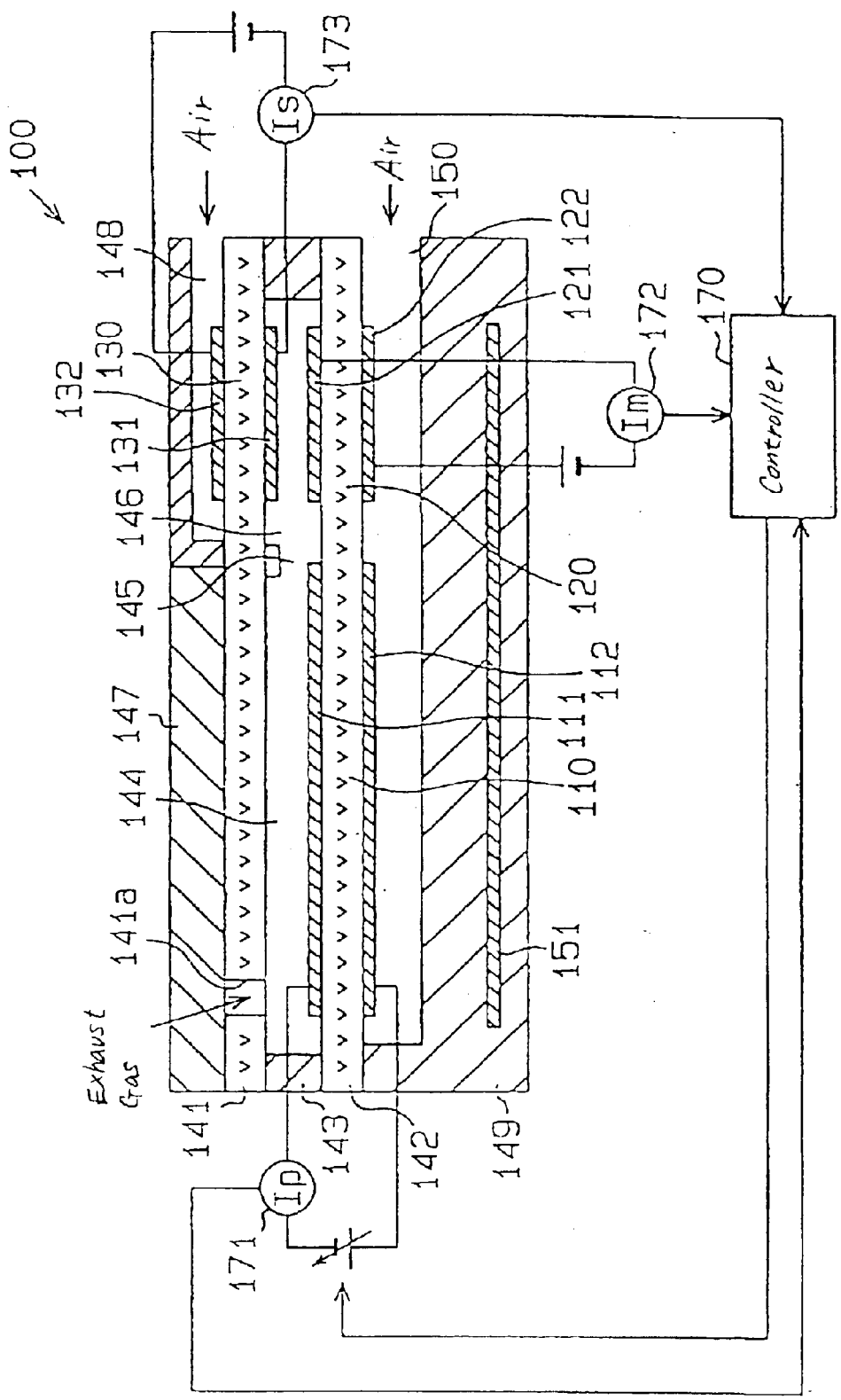
FIG. 1 is a block diagram which shows a gas concentration measuring apparatus according to the first embodiment of the invention.

Referring now to the drawings, wherein like numbers refer to like parts in several views, particularly to FIG. 1, there is shown a gas concentration measuring apparatus according to the first embodiment of the invention which may be used with an automotive control system designed to control the quantity of fuel injected into an internal combustion engine as a function of an output of the gas concentration measuring apparatus under feedback (F/B) control to bring the air-fuel (A/F) ratio into agreement with a target value. The gas concentration measuring apparatus uses a composite limiting current gas sensor which has a three-cell structure capable of measuring concentrations of oxygen ($O_2$) and nitrogen oxide (NOx) contained in exhaust gasses of the internal combustion engine simultaneously.

The gas concentration measuring apparatus, as shown in FIG. 1, generally includes a gas concentration sensor 100, a microcomputer or controller 170, and current detectors 171, 172, and 173 (e.g., ammeters).

The following discussion will refer to an example in which the gas concentration sensor 100 is installed in an exhaust pipe of an automotive internal combustion engine.

The gas concentration sensor 100 includes generally solid electrolyte plates 141 and 142 made of an oxygen ion-conducting material. The solid electrolyte plates 141 and 142 are laid to overlap each other at a given interval through a spacer 143 made of an insulating material such as alumina. The solid electrolyte plate 141 has formed therein a pinhole 141a through which exhaust gasses flowing around the gas concentration sensor 100 are admitted into a first chamber 144. The first chamber 144 communicates with a second chamber 146 through an orifice 145 working as a diffusion path. On the solid electrolyte plate 141, a porous diffusion layer 147 is formed.

The solid electrolyte plate 142 has formed therein a pump cell 110 and a monitor cell 120. The pump cell 110 works to dissociate or ionize and pump thereinto oxygen molecules ($O_2$) contained the exhaust gasses admitted into the first chamber 144 and discharge them for measuring the concentration of oxygen ($O_2$) contained in the exhaust gasses and also to dissociate or ionize and pump oxygen molecules ($O_2$) within an air passage 150 into the first chamber 144 when the concentration of oxygen within the first chamber 144 is lower than a given level for keeping the concentration of oxygen within the first chamber 144 at the given level. The monitor cell 120 works to produce an electromotive force or current upon application of the voltage as a function the concentration of oxygen ($O_2$) within the second chamber 146. The pump cell 110 has a pair of upper and lower electrodes 111 and 112 disposed on opposed surfaces thereof. The upper electrode 111 is exposed to the first chamber 144 and inactive with respect to NOx, that is, hardly decomposes NOx. Similarly, the monitor cell 120 has a pair of upper and lower electrodes 121 and 122 disposed on opposed surfaces thereof. The upper electrode 121 is exposed to the second chamber 146 and inactive with respect to NOx, like the electrode 111. The pump cell 110 and the monitor cell 120 work to pump $O_2$ molecules contained in the exhaust gasses out of the first and second chambers 144 and 146 and discharge them to the air passage 150 through the electrodes 112 and 122.

A sensor cell 130 is formed in the solid electrolyte plate 144 opposite the monitor cell 120 and has a pair of upper and lower electrodes 131 and 132 formed on opposed surfaces thereof. The sensor cell 130 serves to measure the concentration of NOx contained in the exhaust gasses having passed through the pump cell 110 and discharge the oxygen produced when NOx is decomposed within the second chamber 146 to the air passage 148 through the electrode 132.

An insulating layer 149 is disposed on a lower surface, as viewed in the drawing, of the solid electrolyte plate 142 to define the air passage 150. The insulating layer 149 has embedded therein a heater 151 for heating the whole of the sensor 100 up to a given temperature.

In operation, when exhaust gasses containing $O_2$, NOx, $CO_2$, and $H_2O$ is entering the first chamber 144 through the porous diffusion layer 147 and the pinhole 141a and are passing through the pump cell 110, application of voltage to the pump cell 110 through the electrodes 111 and 112 causes the exhaust gasses to undergo dissociation, so that the oxygen is pumped into or out of the first chamber 144 as a function of the concentration of oxygen ($O_2$) within the first chamber 144. Since the upper electrode 111 of the pump cell 110 is, as described above, made of a metal which hardly dissolves NOx, when the concentration of oxygen within the first chamber 144 is higher than a desired level, only $O_2$ molecules within the first chamber 144 are ionized by the pump cell 110 without decomposing NOx, which are, in turn, discharged to the air passage 150. This causes a current (will also referred to as a pump cell current below) to be produced in the pump cell 110 as a function of the oxygen content of the exhaust gasses. EP0 987 546 A2, assigned to the same assignee as that of this application, teaches control of an operation of this type of gas sensor, disclosure of which is incorporated herein by reference.

The $O_2$ molecules in the exhaust gasses are usually not dissociated by the pump cell 110 completely, so that residual $O_2$ molecules flow into the second chamber 146 and reach the monitor cell 120. The application of a given constant voltage to the monitor cell 120 through the electrodes 121 and 122 causes an output (will also be referred to as a monitor cell current below) to be produced as a function of the concentration of the residual oxygen. The application of a given constant voltage to the sensor cell 130 through the electrodes 131 and 132 causes NOx molecules contained in the exhaust gasses to be decomposed or reduced, so that oxygen ions are produced and discharged to the air passage 148, thereby causing a current (also referred to as a sensor cell current or a NOx current below) to flow through the sensor 130 as a function of the concentration of NOx within the second chamber 146.

The controller 170 is implemented by a typical arithmetic logic unit consisting of a CPU, a memory, an A/D converter, a D/A converter, etc.

Power supply circuits are, as clearly shown in the drawing, provided one for each of the pump cell 110, the monitor cell 120, and the sensor cell 130. The power supply circuits include voltage sources for applying the voltages Vp, Vm, and Vs to the pump cell 110, the monitor cell 120, and the sensor cell 130 and the current detectors 171, 172, and 173, respectively. The voltage Vp applied to the pump cell 110 is, as described above, variably controlled by the controller 170. The voltages Vm and Vs applied to the monitor cell 120 and the sensor cell 130 are at constant levels. The current detector 171 measures the pump cell current Ip produced by the pump cell 110 and provides a signal indicative thereof to the controller 170. The current detector 172 measures the monitor cell current Im produced by the monitor cell 120 and provides a signal indicative thereof to the controller 170. The current detector 173 measures the sensor cell current Is produced by the sensor cell 130 and provides a signal indicative thereof to the controller 170.

The controller 170 receives the output from the current detector 171 of the pump cell 110 indicative of the pump cell current Ip and determines the concentration of oxygen ($O_2$) in the exhaust gasses and also determines a value of the pump cell-applied voltage Vp to be applied to the pump cell 110 using a preselected target applying voltage line, as will be described later in detail. The controller 170 also receives the output from the current detector 172 of the monitor cell 120 indicative of the monitor cell current Im to determine the quantity of oxygen remaining in the second chamber 146. The controller 170 also receives the output from the current detector 173 of the sensor cell 130 indicative of the sensor cell current Ip and determines the concentration of NOx contained in the exhaust gasses. The controller 170 may use the monitor cell current Im in correcting the value of the pump cell-applied voltage Vp to the pump cell 110 so as to keep the concentration of oxygen within the second chamber 146 constant or correcting the sensor cell current Ip to eliminate a noise or error added thereto arising from the oxygen remaining within the second chamber 146.

Figure 2A:
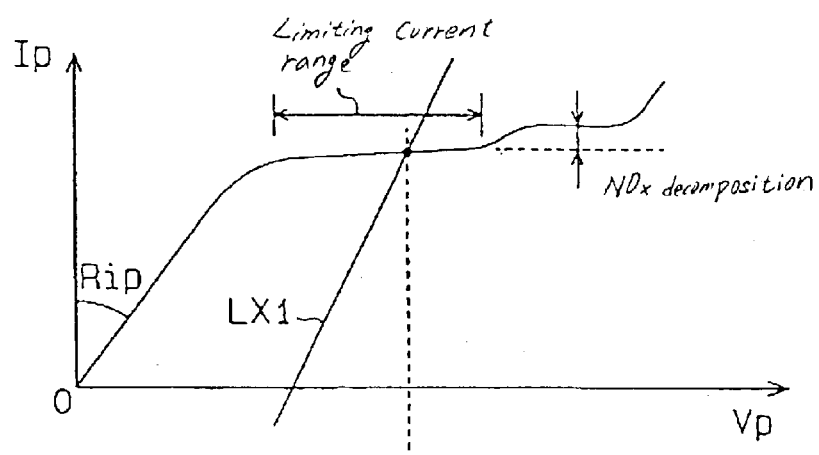
FIG. 2(a) shows a relation between a current output of a pump cell and a value of voltage to be applied to the pump cell and a target applying voltage line used to determine a target value of voltage to be applied to the pump cell.
Figure 2B:
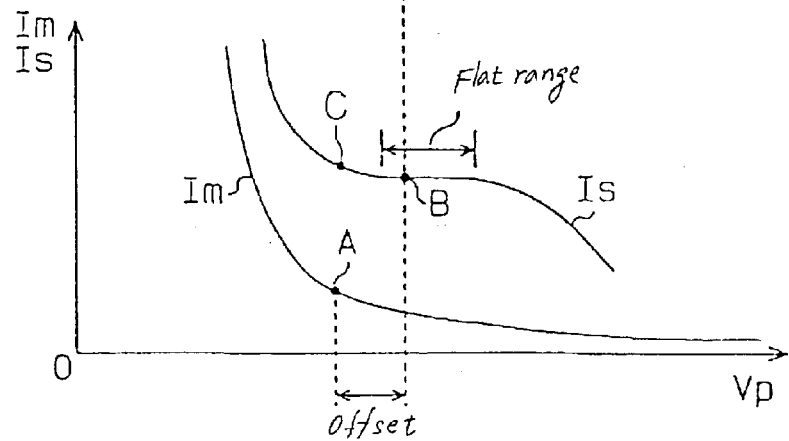
FIG. 2(b) shows relations between a current output of a monitor cell and a value of voltage applied to a pump cell and between a current output of a sensor cell and the value of voltage applied to the pump cell.

FIG. 2(a) shows an example of a Vp-Ip relation between the voltage applied to the pump cell 110 (i.e., the pump cell-applied voltage Vp) and the pump cell current Ip. FIG. 2(b) shows a Vp-Im relation between the pump cell-applied voltage Vp and the monitor cell current Im and a Vp-Is relation between the pump cell-applied voltage Vp and the sensor cell current Is. Note that FIGS. 2(a) and 2(c) illustrate for cases where the concentrations of $O_2$ and NOx are constant, respectively.

The pump cell 110, as described above, produces the pump cell current Ip, changing, as shown in FIG. 2(a), upon application of the pump cell-applied voltage Vp. The pump cell current Ip contains a limiting current. A straight segment of a curve inclined slightly upward with respect to a V-axis (i.e., abscissa axis) indicates a limiting current range in which the limiting current is developed by the pump cell 110. The limiting current range is shifted to the positive side (i.e., a higher level side) of voltage applied to the pump cell 110 as the concentration of oxygen increases. A portion of the curve lower in voltage than the limiting current range indicates a resistance-dependent range. The portion extends upward at an inclination substantially depending upon an impedance Rip of the pump cell 110 (i.e., the solid electrolyte plate 142). The impedance Rip will also be referred to as a pump cell impedance Rip below.

The gas concentration measuring apparatus of this embodiment stores therein a V-I map, as shown in FIG. 2(a), and monitors the pump cell current Ip to determine a target value of the pump cell-applied voltage Vp to be applied to the pump cell 110 by look-up using the V-I map. The V-I map has a target applying voltage line LX1 used in determining the target value of the pump cell-applied voltage Vp. The upper pump cell electrode 111 of the pump cell 110 exposed to the first chamber 144 is, as described above, made of material which hardly decomposes NOx, so that NOx molecules in the exhaust gasses are hardly decomposed, but if the voltage applied to the pump cell 110 exceeds a certain upper limit, it will cause the NOx molecules to be decomposed, thereby producing an error in the pump cell current Ip (i.e., the limiting current) outputted from the pump cell 110. In practice, the target applying voltage line LX1 is so defined as to keep the concentration of oxygen ($O_2$) within the first chamber 144 at a lower level (near the stoichiometric). For instance, the target applying voltage line LX1 is so defined that a small quantity of $O_2$ (e.g., several ppm to several tens ppm) remains in the first chamber 144.

The Vp-Im relation between the pump cell-applied voltage Vp and the monitor cell current Im, as shown in FIG. 2(b), shows that within a range where the pump cell-applied voltage Vp is lower in level, the monitor cell current Im increases greatly with a decrease in pump cell-applied voltage Vp, but it decreases and reaches almost a constant level when the pump cell-applied voltage Vp enters a higher level range. Specifically, as apparent from FIG. 2(a), within the lower pump cell-applied voltage range (i.e., the resistance-dependent range), the pump cell current Ip is lower in level, so that the quantity of oxygen remaining within the first chamber 144 increases. Within the limiting current range of the pump cell 110, the pump cell current Ip is kept almost constant, so that the quantity of oxygen remaining within the first chamber 144 is kept constant. The monitor cell current Im, therefore, changes, as shown in FIG. 2(b), as a function of the pump cell-applied voltage Vp. The curve indicating a change in the monitor cell current Im has an inflection point A at which a rate of the change in the monitor cell current Im changes greatly. The inflection point A may be defined at a point where an inclination of the curve meets a preselected reference rate of the change in the monitor cell current Im.

The Vp-Is relation between the pump cell-applied voltage Vp and the sensor cell current Is has a flat range within which the sensor cell current Is is kept almost constant regardless of the pump cell-applied voltage Vp. Therefore, if the pump cell-applied voltage Vp is adjusted to a level B (will also be referred to as a controlled point below), it is possible to measure the concentration of NOx in the exhaust gasses accurately. In this case, the inflection point A of the Vp-Im curve is away from the flat range of the sensor cell current Is. Specifically, the inflection point A is offset from the controlled point B. The offset between the inflection point A and the controlled point B is the value fixed for each type of gas sensor.

A change in impedance Rip of the pump cell 110 arising from a unit-to-unit difference or aging of the gas concentration sensor 100 will be described below with reference to FIGS. 3(a) to 4(b). Solid lines in FIGS. 3(a) to 4(b) indicate the V-I curves as illustrated in FIGS. 2(a) and 2(b). Broken lines indicate V-I curves when the pump cell impedance Rip increases or decreases.

Figure 3A:
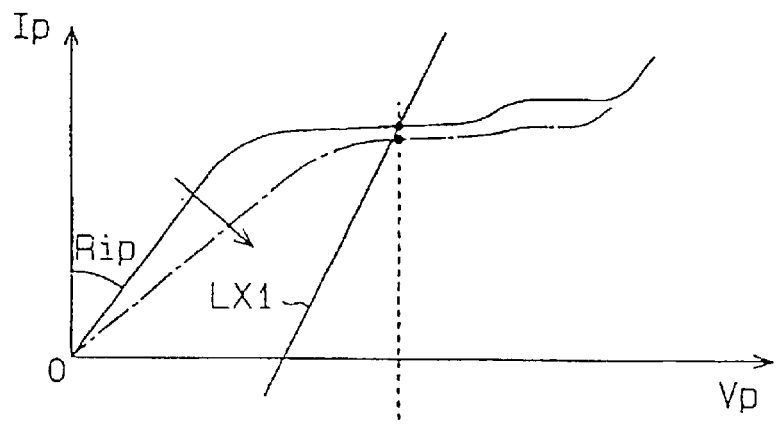
FIG. 3(a) shows a relation between a current output of a pump cell and a value of voltage to be applied to the pump cell which is shifted due to, for example, aging of a gas concentration sensor.
Figure 3B:
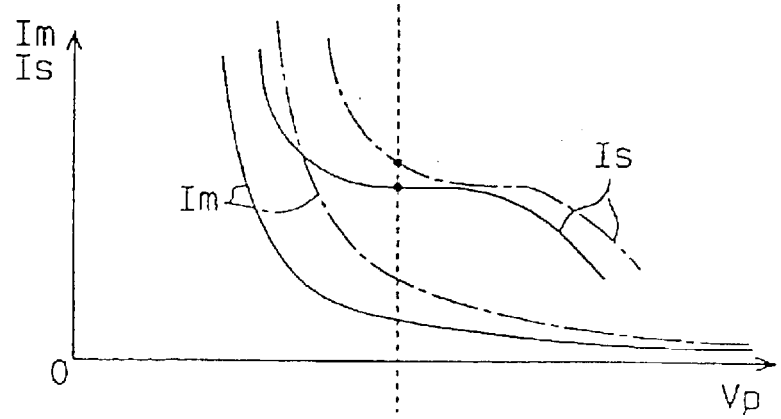
FIG. 3(b) shows relations between a current output of a monitor cell and a value of voltage applied to a pump cell and between a current output of a sensor cell and the value of voltage applied to the pump cell which are shifted due to, for example, aging of a gas concentration sensor.

When the impedance Rip of the pump cell 110 increases, it will cause the inclination of the Vp-Ip curve of FIG. 3(a) to decrease, so that the pump cell current Ip decreases. This causes the quantity of oxygen remaining within the first chamber 144 to increase. The monitor cell current Is and the sensor cell current Is, thus, change, as indicated by the broken lines of FIG. 3(b). Specifically, the sensor cell current Is increases, thus resulting in an increase in error in determining the concentration of NOx using the senor cell current Is.

Figure 4A:
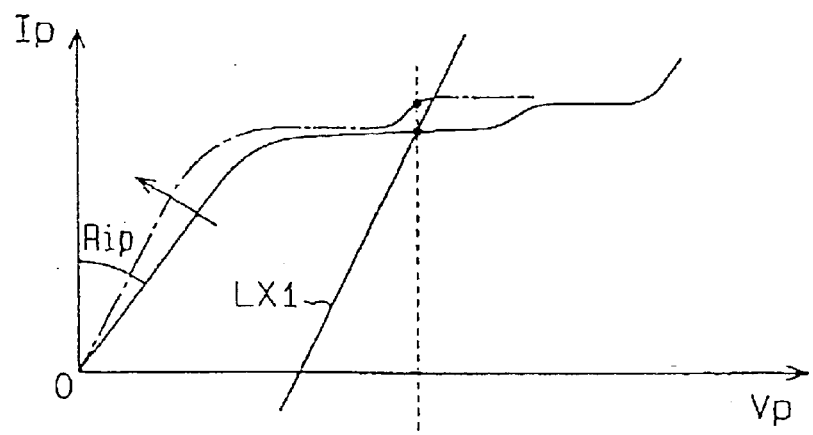
FIG. 4(a) shows a relation between a current output of a pump cell and a value of voltage to be applied to the pump cell which is shifted due to a change in impedance of a gas concentration sensor.
Figure 4B:
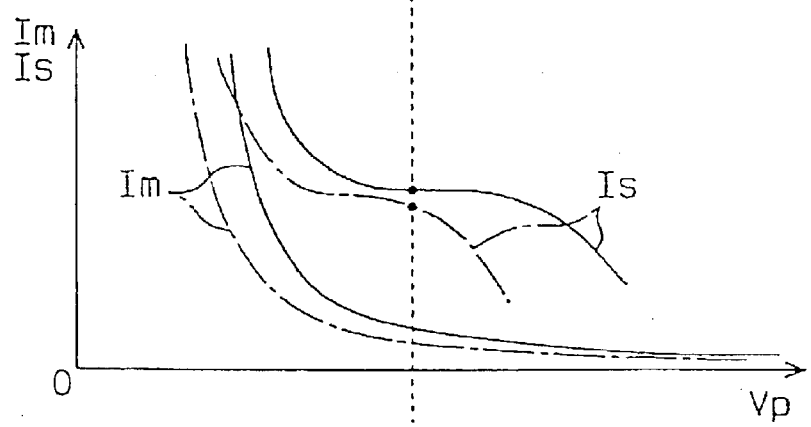
FIG. 4(b) shows relations between a current output of a monitor cell and a value of voltage applied to a pump cell and between a current output of a sensor cell and the value of voltage applied to the pump cell which are shifted due to an increase in quantity of oxygen remaining within a gas chamber of a gas concentration sensor.

Conversely, when the pump cell impedance Rip is decreased, it will cause the inclination of the Vp-Ip curve to increase, as indicated by the broken line in FIG. 4(a), so that the pump cell current Ip increases. This causes the quantity of oxygen remaining within the first chamber 144 to decrease. The monitor cell current Is and the sensor cell current Is, thus, change, as indicated by the broken lines of FIG. 4(b). Specifically, the sensor cell current Is decreases, thus resulting in an increase in error in determining the concentration of NOx using the senor cell current Is.

As apparent from the above discussion, an undesirasble change in impedance Rip of the pump cell 110 results in a decreased accuracy of measuring the concentration of NOx using the sensor cell current Is produced by the sensor cell 130. This is due to the fact that the change in pump cell impedance Rip results in a shift in the flat range of the sensor cell current Is, which leads to an increase in error of the sensor cell current Is. In order to avoid this problem, the gas concentration measuring apparatus of this embodiment is designed base on the fact that a correlation between the inflection point A of the Vp-Im curve indicating a change in the monitor cell current Im in terms of a change in the pump cell-applied voltage Vp and the flat range of the sensor cell current Is is fixed regardless of a change in pump cell impedance Rip and works to control the pump cell-applied voltage Vp based on the location of the inflection point A of the Vp-Im curve.

Specifically, a change in quantity of oxygen remaining in the first chamber 44 results in a change in the inflection point A of the Vp-Im curve, that is, a difference between the inflection point A and a value of the pump cell-applied voltage Vp applied to the pump cell 110. The gas concentration measuring apparatus is designed to use the difference between the inflection point A and the value of the pump cell-applied voltage Vp applied to the pump cell 110 to change the value of the pump cell-applied voltage Vp or correct the V-I map so that the sensor cell current Is is developed within the flat range, thereby eliminating the error in determining the concentration of NOx.

Figure 5:
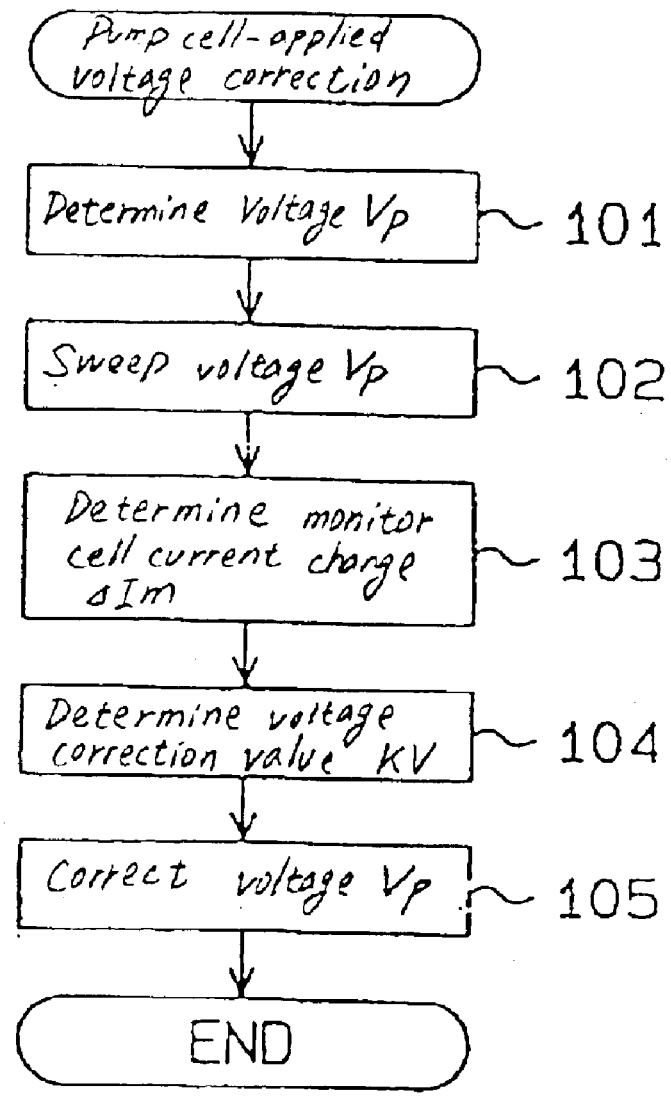
FIG. 5 is a flowchart of a main program to correct a value of voltage to be applied to a pump cell.

Control of the pump cell-applied voltage Vp to be applied to the pump cell 110 will be described below in detail. FIG. 5 is a flowchart of a program to correct the pump cell-applied voltage Vp which is executed by the controller 170 at a regular interval of, for example, several seconds. This pump cell-applied voltage correction time is shifted from a gas concentration measuring time when the concentration of NOx is measured cyclically. Specifically, during the gas concentration measuring time, the pump cell-applied voltage Vp is determined as a function of the pump cell current Ip using the target applying voltage line LX1 to measure the concentration of NOx in a cycle of, for example, 4 msec. When the pump cell-applied voltage correction time is entered, the gas concentration measuring apparatus works to prohibit the measurement of the concentration of NOx and correct the pump cell-applied voltage Vp as a function of a unit-to-unit difference or degree of aging of the gas concentration sensor 100.

After entering the program of FIG. 5, the routine proceeds to step 101 wherein an initial value of the pump cell-applied voltage Vp is determined by look-up using the target applying voltage line LX1 of FIG. 2(a) as a function of the pump cell current Ip as measured instantaneously and applied to the pump cell 110.

The routine proceeds to step 102 wherein the pump cell-applied voltage Vp is swept from the initial value at a given amplitude ΔV both to positive and negative sides (i.e., higher and lower level sides). The routine proceeds to step 103 wherein a change ΔIm in the monitor cell current Im resulting from the sweep of the pump cell-applied voltage Vp is measured. The sweep of the pump cell-applied voltage Vp is performed preferably in a cycle of 200 msec. or less (i.e., 5 Hz or more), and more preferably in a cycle of 100 msec. or less (i.e., 10 Hz or more).

Figure 6:
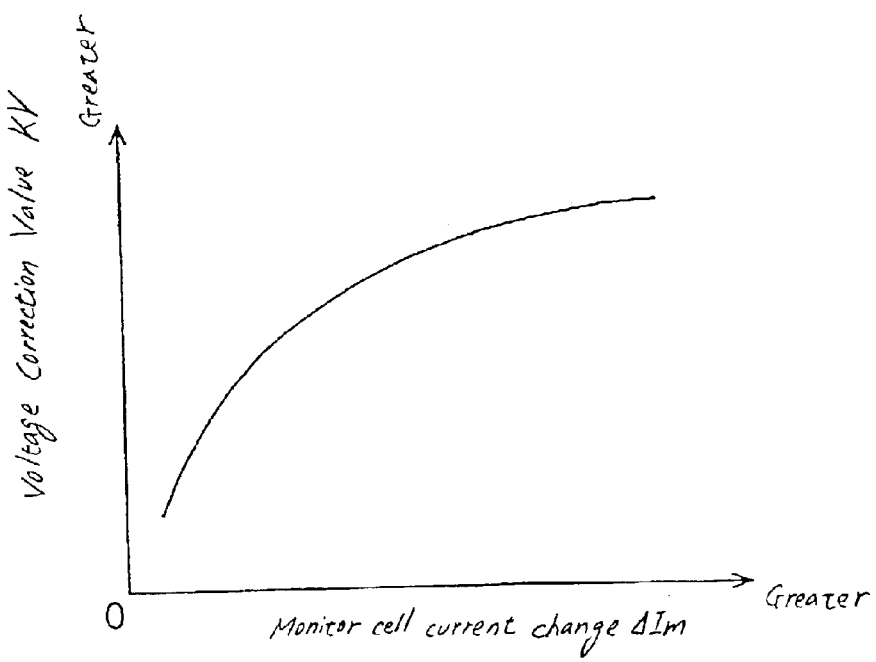
FIG. 6 is a map which indicates a correction value used in correcting a voltage to be applied to a pump cell, determined as a function of a change in current output of a monitor cell.

The routine proceeds to step 104 wherein a voltage correction value KV is determined as a function of the monitor cell current change ΔIm as measured in step 103 by look-up using a map as illustrated in FIG. 6. Finally, the routine proceeds to step 105 wherein the target applying voltage line LX1 is corrected using the voltage correction value KV to correct the pump cell-applied voltage Vp.

The voltage correction value KV may alternatively be stored in a backup memory such as a backup RAM or a flash ROM or used in correcting the target applying voltage line LX1. For instance, the voltage correction value KV are stored in the memory over a plurality of cycles. If some of the voltage corrections values KV stored in the memory fall within a given range, the controller 170 may determine that the target applying voltage line LX1 or the pump cell-applied voltage VP should be corrected. This minimizes errors in correcting the pump cell-applied voltage Vp.

In the program of FIG. 5, a determination of whether the pump cell-applied voltage Vp should be corrected or not may be made by measuring changes in monitor cell current Im arising from the sweep of the pump cell-applied voltage Vp to the positive side and to the negative side and determining whether they are substantially identical with each other or not. Specifically, in a case where the pump cell-applied voltage Vp is set within a flat range of the monitor cell current Im and far from the inflection point A, the changes in monitor cell current Im arising from the sweep of the pump cell-applied voltage Vp both to the positive and negative sides are usually small, that is, substantially identical with each other. If this is one of original sensor characteristics of the gas sensor 100, the controller 170 may decide that the pump cell-applied voltage Vp needs not be corrected when the changes in monitor cell current Im arising from the sweep of the pump cell-applied voltage Vp to the positive side and to the negative side are substantially identical with each other and that the pump cell-applied voltage Vp should be corrected when a difference between the changes in monitor cell current Im is greater than a preselected value.

The operation of the controller 170 executed in the program of FIG. 5 will be exemplified below.

Figure 7:
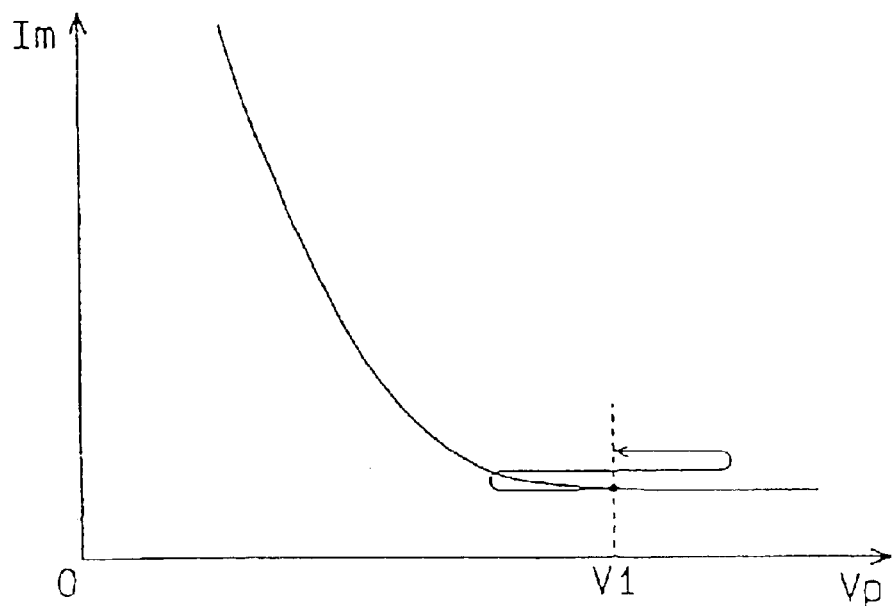
FIG. 7 shows a change in a current output of a monitor cell upon a sweep of voltage applied to a pump cell.

It is assumed that the pump cell-applied voltage Vp is initially set to a voltage value V1 as shown in FIG. 7. The pump cell-applied voltage Vp is swept from the voltage value V1 both to the positive and negative sides temporarily. Specifically, a sawtooth voltage is applied to the pump cell 110 for a given short period of time. If there is a unit-to-unit variation in characteristic of the gas concentration sensor 100 or the gas concentration sensor 100 has aged, the inflection point A of the monitor cell current Im is close to the voltage value V1. The application of the sawtooth voltage to the pump cell 110, thus, causes the monitor cell current Im to change greatly.

Figure 8A:
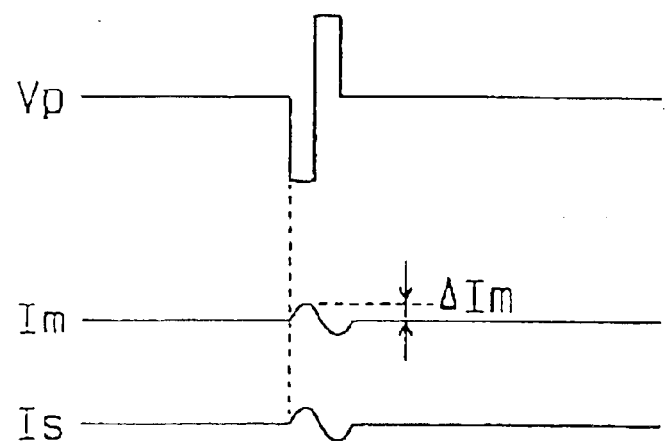
FIG. 8(a) shows changes in current outputs of a monitor cell and a sensor cell arising from a sweep of voltage applied to a pump cell when a target value of voltage to be applied to the pump cell needs not be corrected.

For example, if the inflection point A is not close to the voltage value V1 the sweep of the pump cell-applied voltage Vp result in, as shown in FIG. 8(a), small changes in the monitor cell current Im and the sensor cell current Is. In this case, the controller 170 decides that the pump cell-applied voltage Vp needs not be corrected and applies it directly to the pump cell 110.

Figure 8B:
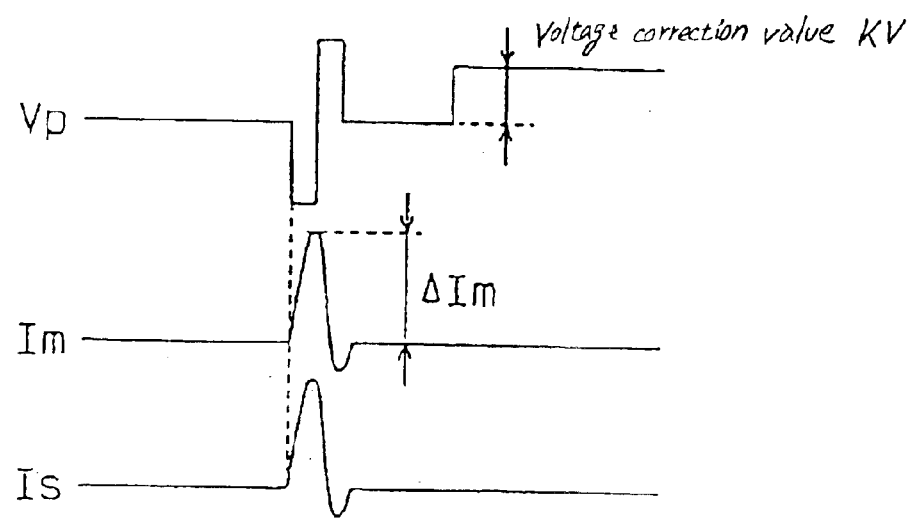
FIG. 8(b) shows changes in current outputs of a monitor cell and a sensor cell arising from a sweep of voltage applied to a pump cell in a case where it is determined that a target value of voltage to be applied to the pump cell should be corrected.

Alternatively, if the inflection point A is close to the voltage value V1 it results in, as shown in FIG. 8(b), a great difference between the changes in monitor cell current Im arising from the sweep of the pump cell-applied voltage Vp to the positive side and to the negative side. In this case, the controller 170 decides that the pump cell-applied voltage Vp should be corrected and adds the voltage correction value KV to the pump cell-applied voltage Vp to shift the pump cell-applied voltage Vp away from the inflection point A of the monitor cell current Im.

The sweep of the pump cell-applied voltage is, as described above, made both to the positive and negative sides from the voltage value V1 thereby enabling a positional relation between a change in the pump cell-applied voltage Vp and the inflection point A of the monitor cell current Im to be determined accurately instantaneously. It is, therefore, possible to locate the inflection point A of the monitor cell current Im accurately regardless of a change thereof. The sweep to the positive and negative sides quickens returning of the monitor cell current Im and the sensor cell current Is.

Figure 9:
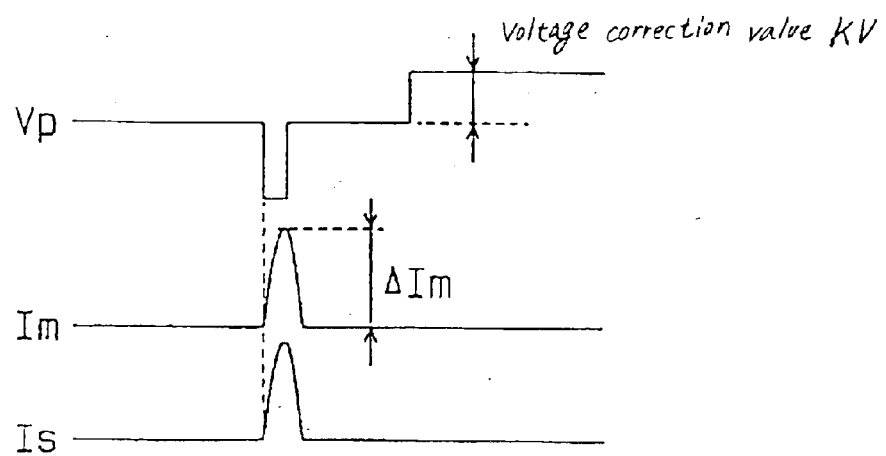
FIG. 9 shows changes in current outputs of a monitor cell and a sensor cell arising from a sweep of voltage applied to a pump cell to one of lower and higher level sides.

The sweep of the pump cell-applied voltage Vp may alternatively be made to either of the positive and negative sides from the voltage value V1. For instance, the pump cell-applied voltage Vp may be, as shown in FIG. 9, swept only to a lower level side to determine a change ΔIm in monitor cell current Im for use in determining the voltage correction value KV for the pump cell-applied voltage Vp. This also enables the sensor cell current Is to be measured within the flat range of the Vp-Is curve, as shown in FIG. 2(b), thereby keeping the accuracy of measuring the concentration of NOx free from the unit-to-unit difference and/or aging of the gas concentration sensor 100.

The monitor cell current Im and the sensor cell current Is produced at the time of the sweep of the pump cell-applied voltage Vp may be filtered to blur them in a waveform. This enables the concentration of oxygen and NOx to be measured using the monitor cell current Im and the sensor cell current Is free from the sweep of the pump cell-applied voltage Vp during the pump cell-applied voltage correction time.

The pump cell-applied voltage Vp may be swept to the positive and negative sides at difference amplitudes. For instance, the pump cell-applied voltage Vp is first swept from the voltage value V1 at a greater amplitude, as indicated at numeral 600 in FIG. 10, after which it is swept at a smaller amplitude, as indicated at numeral 700 in FIG. 10. The order may be reversed. Use of the different amplitudes enables how far from the flat range of the senor cell current Is the inflection point of the monitor cell current Im lies to be determined. The sweep of the pump cell-applied voltage Vp may also be made at more than two different amplitudes.

A gas concentration measuring apparatus of the second embodiment will be described below which is different from the first embodiment in that the pump cell-applied voltage Vp is corrected using the sensor cell current Is, not the monitor cell current Im. Other arrangements are identical, and explanation thereof in detail will be omitted here.

Referring back to FIG. 2(b), like the Vp-Im curve of the monitor cell current Im, the Vp-Is curve of the sensor cell current Is also has an inflection point C at which the rate of a change in the sensor cell current Is changes greatly. The gas concentration measuring apparatus of this embodiment is designed to control the pump cell-applied voltage Vp based on a locational relation between the inflection point C and the flat range where the sensor cell current Is hardly changes free from a change in the pump cell-applied voltage Vp. Specifically, a change in quantity of oxygen remaining within the first chamber 144 results in a shift in the inflection point C. The pump cell-applied voltage Vp is corrected as a function of the shift in the inflection point C so that a target value of the pump cell-applied voltage Vp may lie within the flat range. This keeps the accuracy of measuring the concentration of NOx using the sensor cell current Is.

Figure 11:
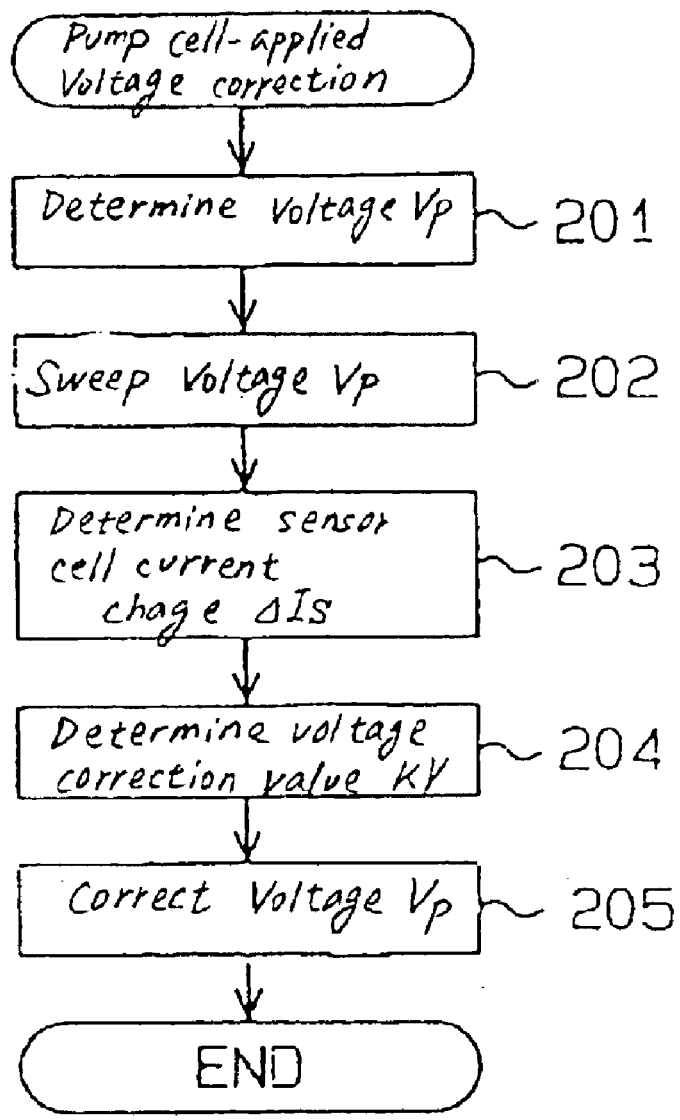
FIG. 11 is a flowchart of a program executed in the second embodiment to correct a value of voltage to be applied to a pump cell.

FIG. 11 is a flowchart of a pump cell-applied voltage correcting program executed in the controller 170 of the gas concentration sensor of the second embodiment.

First, in step 201, an initial value of the pump cell-applied voltage Vp is determined by look-up using the target applying voltage line LX1 of FIG. 2(a) as a function of the pump cell current Ip as measured instantaneously. The pump cell-applied voltage Vp is then applied to the pump cell 110.

Next, the routine proceeds to step 202 wherein the pump cell-applied voltage Vp is swept over a given amplitude ΔV both to positive and negative sides. The routine proceeds to step 203 wherein a change ΔIs in the sensor cell current Is arising from the sweep of the pump cell-applied voltage Vp is measured. The sweep of the pump cell-applied voltage Vp is performed preferably in a cycle of 200 msec. or less (i.e., 5 Hz or more), and more preferably in a cycle of 100 msec. or less (i.e., 10 Hz or more).

Figure 12:
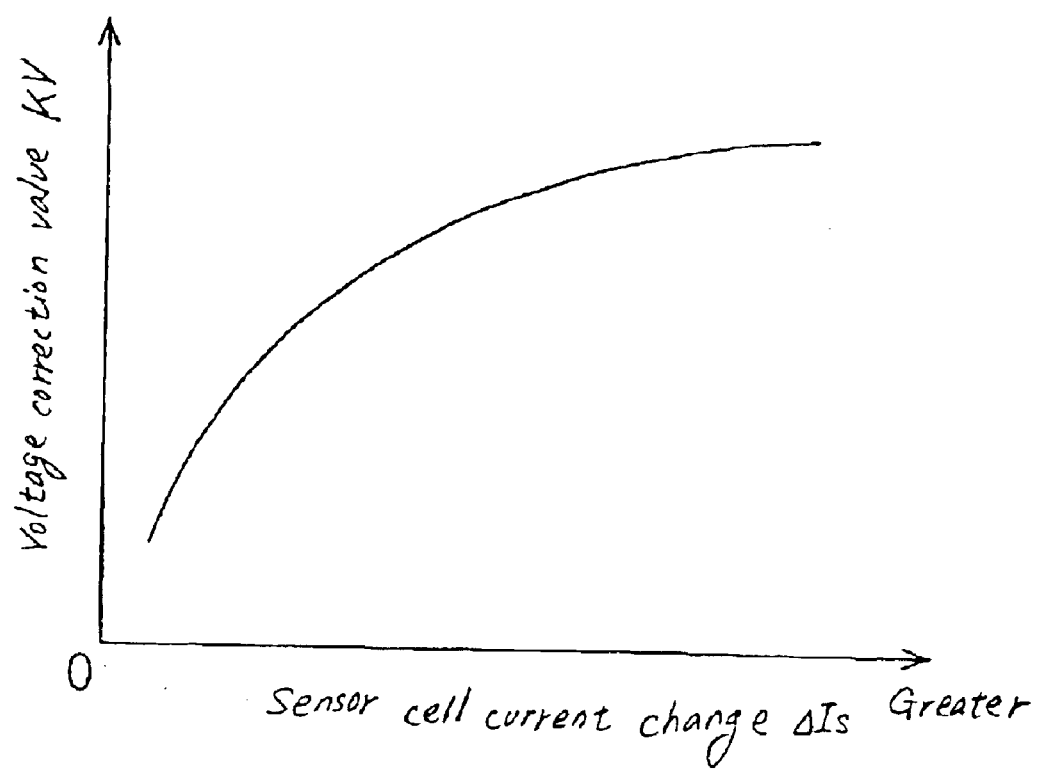
FIG. 12 is a map which indicates a correction value used in correcting a voltage to be applied to a pump cell, determined as a function of a change in current output of a sensor cell.

The routine proceeds to step 204 wherein a voltage correction value KV is determined as a function of the sensor cell current change ΔIs as measured in step 203 by look-up using a map as illustrated in FIG. 12. Finally, the routine proceeds to step 205 wherein the pump cell-applied voltage Vp is corrected using the voltage correction value KV.

The voltage correction value KV may alternatively be stored in a backup memory such as a backup RAM or a flash ROM or used in correcting the target applying voltage line LX1. In this case, when the gas concentration measuring time is entered to measure the concentration of NOx, the controller 170 corrects the pump cell-applied voltage Vp using the voltage correction value KV to determine a final voltage to be applied to the pump cell 110 or determines the final voltage using the corrected target applying voltage line LX1.

In the program of FIG. 11, a determination of whether the pump cell-applied voltage Vp should be corrected or not may be made by measuring changes in sensor cell current Is arising from the sweep of the pump cell-applied voltage Vp to the positive side and to the negative side and determining whether they are substantially identical with each other or not. Specifically, in a case where the pump cell-applied voltage Vp is set within the flat range of the sensor cell current Is and far from the inflection point C, the changes in sensor cell current Is arising from the sweep of the pump cell-applied voltage Vp both to the positive and negative sides are usually small. If this is one of original sensor characteristics of the gas sensor 100, the controller 170 may decide that the pump cell-applied voltage Vp needs not be corrected when the changes in sensor cell current Is arising from the sweep of the pump cell-applied voltage Vp to the positive side and to the negative side are substantially identical with each other and that the pump cell-applied voltage Vp should be corrected when a difference between the changes in sensor cell current Is is smaller than a given value.

The operation of the controller 170 executed in the program of FIG. 11 will be exemplified below.

It is assumed that the pump cell-applied voltage Vp is initially set to a voltage value V1 as shown in FIG. 7. The pump cell-applied voltage Vp is swept from the voltage value V1 both to the positive and negative sides temporarily in the same manner as described in the first embodiment. Specifically, a sawtooth voltage is applied to the pump cell 110 for a short period of time. If there is a unit-to-unit difference of the gas concentration sensor 100 or the gas concentration sensor 100 has aged, the inflection point C of the sensor cell current Is is close to the voltage value V1. The application of the sawtooth voltage to the pump cell 110, thus, causes the sensor cell current Is to change greatly.

Figure 13A:
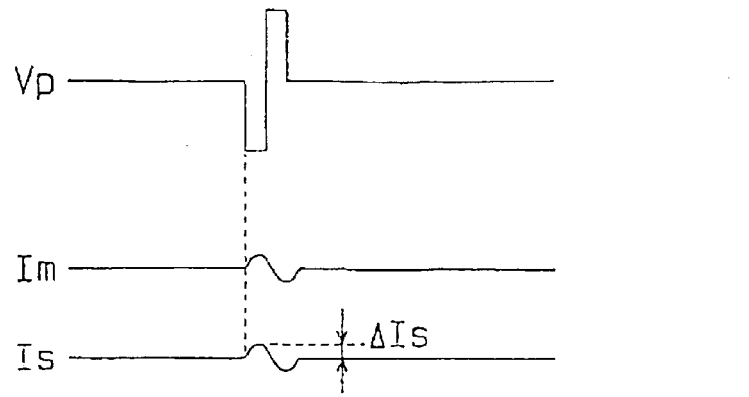
FIG. 13(a) shows changes in current output of a monitor cell and a sensor cell arising from a sweep of voltage applied to a pump cell when a target value of voltage to be applied to the pump cell needs not be corrected in the second embodiment.

For example, if the inflection point C does not lie close to the voltage value V1 the sweep of the pump cell-applied voltage Vp result in, as shown in FIG. 13(a), small changes in the monitor cell current Im and the sensor cell current Is. In this case, the controller 170 decides that the pump cell-applied voltage Vp needs not be corrected and applies it directly to the pump cell 110.

Figure 13B:
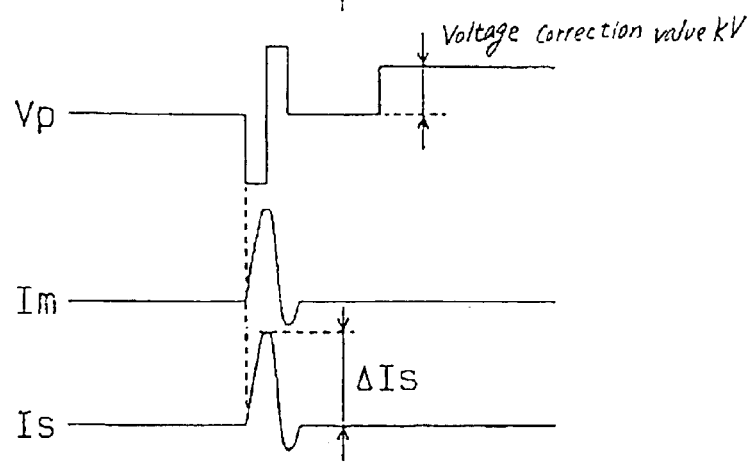
FIG. 13(b) shows changes in current outputs of a monitor cell and a sensor cell arising from a sweep of voltage applied to a pump cell in a case where it is determined that a target value of voltage to be applied to the pump cell should be corrected in the second embodiment.

Alternatively, if the inflection point C lies close to the voltage value V1 it results in, as shown in FIG. 13(b), a great difference between the changes in each of the monitor cell current Im and the sensor cell current Is arising from the sweep of the pump cell-applied voltage Vp to the positive side and to the negative side. In this case, the controller 170 decides that the pump cell-applied voltage Vp should be corrected and adds the voltage correction value KV to the pump cell-applied voltage Vp to shift the pump cell-applied voltage Vp away from the inflection point C of the sensor cell current Is (i.e., to the positive side in the drawing).

The sweep of the pump cell-applied voltage is, as described above, made both to the positive and negative sides from the voltage value V1 thereby enabling a positional relation between an initial value of the pump cell-applied voltage Vp and the inflection point C of the sensor cell current Is to be determined accurately nstantaneously. It is, therefore, possible to locate the inflection point C of the sensor cell current Is accurately regardless of a change thereof. The sweep to the positive and negative sides quickens returning of the pump cell-applied voltage Vp to a target one.

Figure 14:
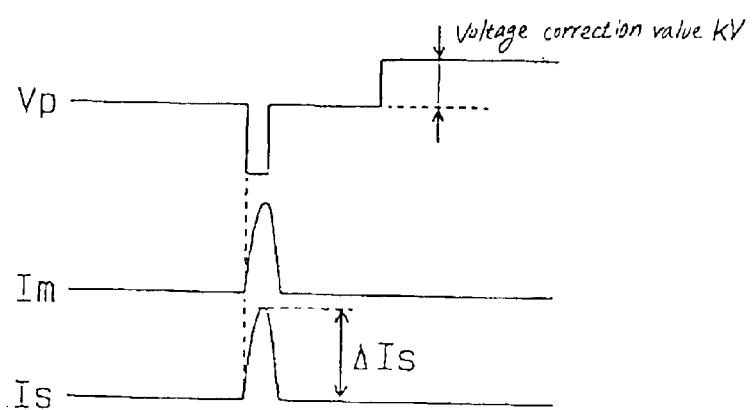
FIG. 14 shows changes in current output of a monitor cell and a sensor cell arising from a sweep of voltage applied to a pump cell to one of lower and higher level sides.

The sweep of the pump cell-applied voltage Vp may alternatively be made to either of the positive and negative sides from the voltage value V1. For instance, the pump cell-applied voltage Vp may be, as shown in FIG. 14, swept only to a lower level side to determine a change ΔIs in sensor cell current Is for use in determining the voltage correction value KV for the pump cell-applied voltage Vp.

Figure 10:
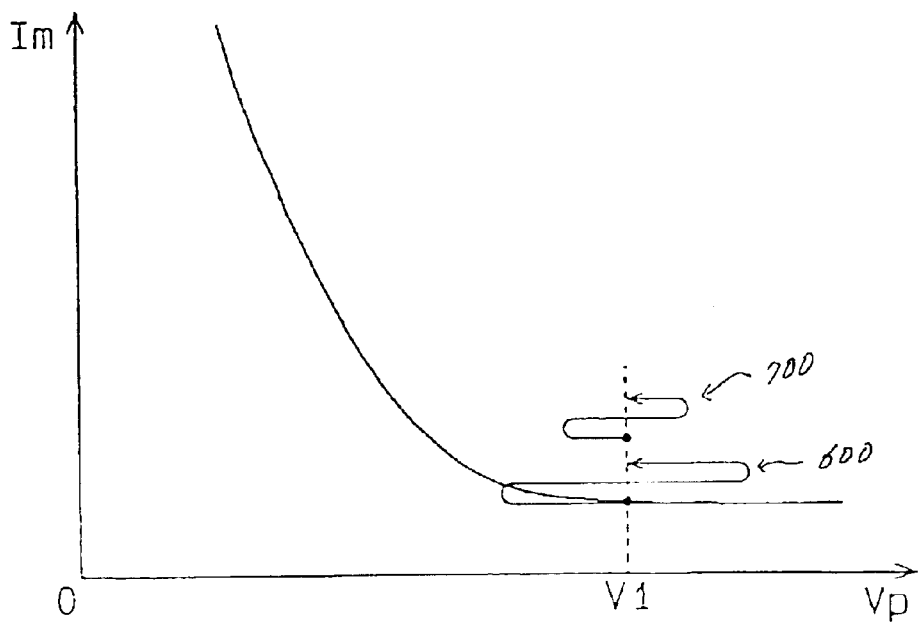
FIG. 10 shows changes in current output of a monitor cell upon sweeps of voltage applied to a pump cell at different amplitudes.

The pump cell-applied voltage Vp may be swept to the positive and negative sides at difference amplitudes, as described with reference to FIG. 10.

The monitor cell current Im and the sensor cell current Is produced at the time of the sweep of the pump cell-applied voltage Vp may be, like the first embodiment, filtered to blur them in a waveform. This enables the concentration of oxygen and NOx to be measured using the monitor cell current Im and the sensor cell current Is free from the sweep of the pump cell-applied voltage Vp during the pump cell-applied voltage correction time.

A gas concentration measuring apparatus of the third embodiment will be described below which is different from the first embodiment in that the pump cell-applied voltage Vp is controlled so as to keep the change ΔIm in the monitor cell current Im constant. Other arrangements are identical, and explanation thereof in detail will be omitted here.

Figure 15:
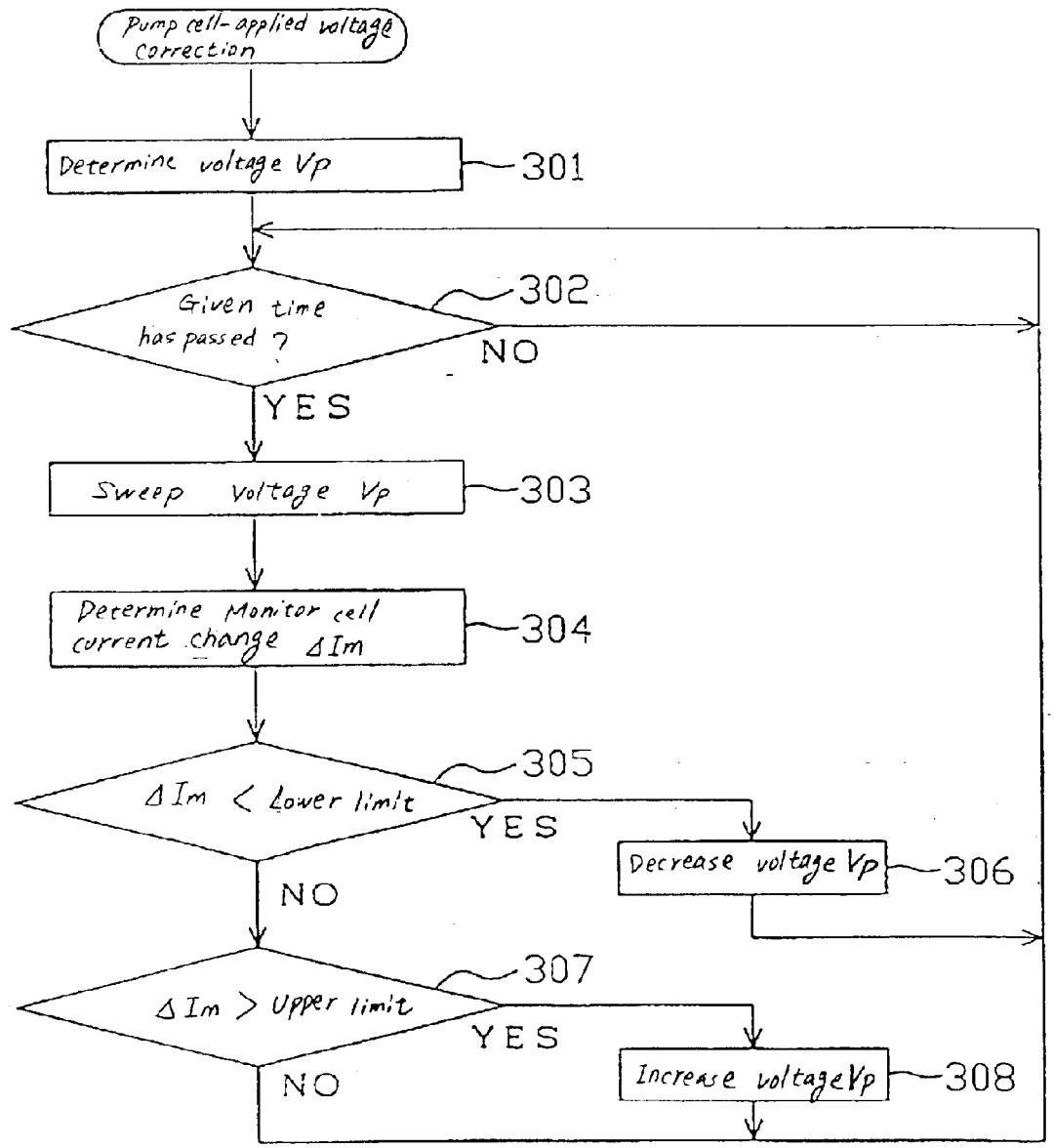
FIG. 15 is a flowchart of a program executed in the third embodiment to correct a value of voltage to be applied to a pump cell.

FIG. 15 shows a flowchart of a pump cell-applied voltage control program executed in the controller 170.

After entering the program, the routine proceeds to step 301 wherein an initial value of the pump cell-applied voltage Vp is determined by look-up using the target applying voltage line LX1 of FIG. 2(a) as a function of the pump cell current Ip as measured instantaneously and applied to the pump cell 110.

The routine proceeds to step 302 wherein it is determined whether a preselected period of time has expired or not. Specifically, it is determined whether a correction time when the pump cell-applied voltage Vp should be corrected has been reached or not. If a YES answer is obtained, then the routine proceeds to step 303 wherein the pump cell-applied voltage Vp is swept over a given amplitude ΔV both to positive and negative sides. The routine proceeds to step 304 wherein a change ΔIm in the monitor cell current Im arising from the sweep of the pump cell-applied voltage Vp is measured. The sweep of the pump cell-applied voltage Vp is performed preferably in a cycle of 200 msec. or less (i.e., 5 Hz or more), and more preferably in a cycle of 100msec. or less (i.e., 10 Hz or more).

The routine proceeds to step 305 wherein it is determined whether the monitor cell current change ΔIm is lower than a lower limit of a given monitor cell current-controlled range or not. If a YES answer is obtained meaning that the pump cell-applied voltage Vp is far from the inflection point A of the monitor cell current Im undesirably, then the routine proceeds to step 306 wherein a negative correction value is provided which is used to decrease a value of the pump cell-applied voltage Vp determined as a function of the pump cell current Ip by look-up using the target applying voltage line LX1.

Alternatively, if a NO answer is obtained in step 305 meaning that the monitor cell current change ΔIm is higher than the lower limit of the monitor cell current-controlled range, then the routine proceeds to step 307 wherein it is determined whether the monitor cell current change ΔIm is higher than an upper limit of the monitor cell current-controlled range or not. If a YES answer is obtained meaning that the pump cell-applied voltage Vp is close to the inflection point A of the monitor cell current Im undesirably, then the routine proceeds to step 308 wherein a positive correction value is provided which is used to increase a value of the pump cell-applied voltage Vp determined as a function of the pump cell current Ip by look-up using the target applying voltage line LX1.

The operation of the controller 170 executed in the program of FIG. 15 will be exemplified below.

Figures 16A, 16B, 16C:
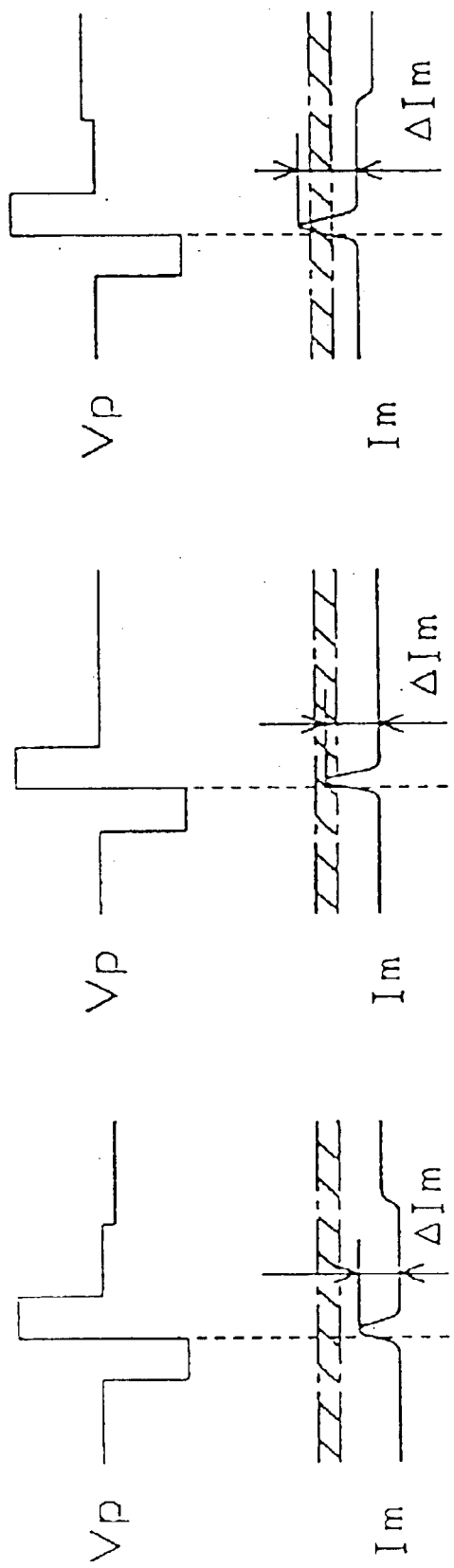
FIGS. 16(a), 16(b), and 16(c) show changes in current output of a monitor cell brought into a desired controlled range by an operation of the program of FIG. 15.

FIG. 16(a) illustrates for the case where the pump cell-applied voltage Vp is far from the inflection point A, so that the monitor cell current change ΔIm is lower than the lower limit of the monitor cell current-controlled range. In this case, a YES answer is obtained in step 305 of FIG. 15. The value of the pump cell-applied voltage Vp to be applied to the pump cell 110 is decreased in step 306. FIG. 16(b)

illustrates for the case where the pump cell-applied voltage Vp lies at a desired distance from the inflection point A, so that the monitor cell current change ΔIm lies within the monitor cell current-controlled range. In this case, NO answers are obtained both in steps 305 and 307. The pump cell-applied voltage Vp as determined using the target applying voltage line LX1 is, therefore, applied directly to the pump cell 110. FIG. 16(c) illustrates for the case where the pump cell-applied voltage Vp is close to the inflection point A, so that the monitor cell current change ΔIm is higher than the upper limit of the monitor cell current-controlled range. In this case, a YES answer is obtained in step 307. The value of the pump cell-applied voltage Vp to be applied to the pump cell 110 is increased in step 308.

The correction values provided in steps 306 and 307 may be set to fixed values selected from between 1 mV and 100 mV or alternatively determined as a function of the monitor cell current change ΔIm. The monitor cell current-controlled range is preferably determined depending upon the level of the monitor cell current Im and, for example, 0.1 µA to 0.2 µA.

As apparent from the above discussion, the gas concentration measuring apparatus of this embodiment works to correct the value of the pump cell-applied voltage Vp so as to keep the monitor cell current change ΔIm within the target range, thereby keeping the accuracy of measuring the concentration of gasses free from the unit-to-unit variation and aging of the gas concentration sensor 100.

The gas concentration measuring apparatus may alternatively be designed to monitor a change in the sensor cell current Is and use it in place of the monitor cell current change ΔIm to correct the value of the pump cell-applied voltage Vp in the same manner as described above.

A gas concentration measuring apparatus according to the fourth embodiment of the invention will be described below which is designed to determine the degree of deterioration of the gas concentration sensor 100 based on the inflection point A of the monitor cell current Im.

Figure 17A:
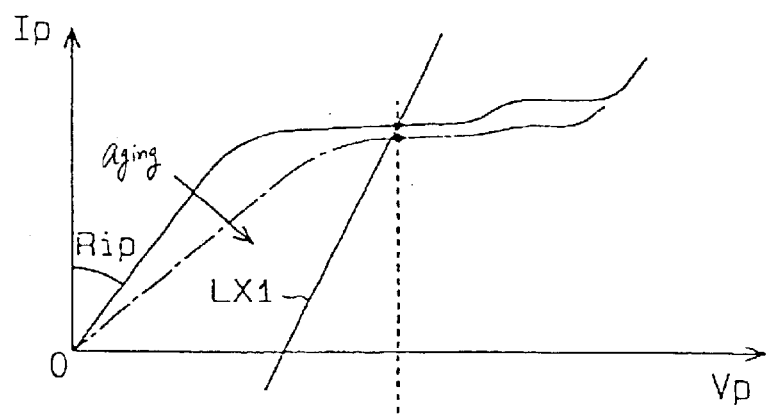
FIG. 17(a) shows a relation between a current output of a pump cell and a value of voltage to be applied to the pump cell which is shifted due to, for example, aging of a gas concentration sensor.
Figure 17B:
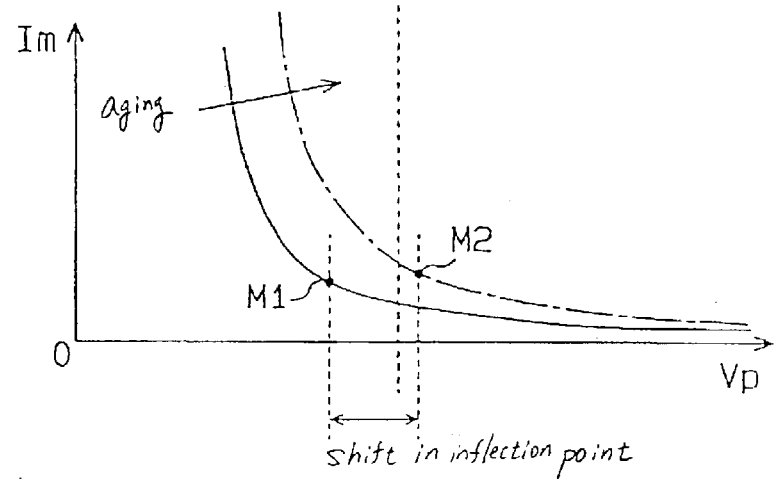
FIG. 17(b) shows a shift in current output of a monitor cell current airing from aging of a gas concentration sensor.

Usually, the aging or deterioration of the gas concentration sensor 100 results in a shift in the inflection point of the monitor cell current Im. The more the deterioration, the more the shift in the inflection point. Specifically, the inflection point of the monitor cell current Im is shifted to a higher level side of the pump cell-applied voltage Vp as the deterioration of the gas concentration sensor 100 increases. For instance, the inflection point of the monitor cell current Im is, as illustrated in FIG. 17(b), shifted from M1 to M2 as the deterioration of the gas concentration sensor 100 increases.

The controller 170 works to sweep the pump cell-applied voltage Vp temporarily to at least one of the positive and negative sides and use a resulting value of the monitor cell current Im to determine the degree of deterioration of the gas concentration sensor 100. For example, when the value of the monitor cell current Im has become greater, the controller 170 decides that the inflection point of the monitor cell current Im is undesirably close to the value of the pump cell-applied voltage Vp as determined using the target applying voltage line LX1 and outputs an alarm signal when the degree of the deterioration increases out of an allowable range.

Figure 18A:
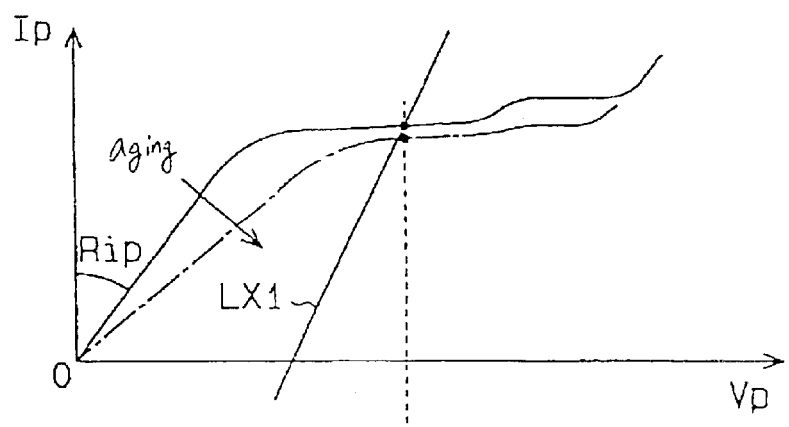
FIG. 18(a) shows a relation between a current output of a pump cell and a value of voltage to be applied to the pump cell which is shifted due to, for example, aging of a gas concentration sensor.
Figure 18B:
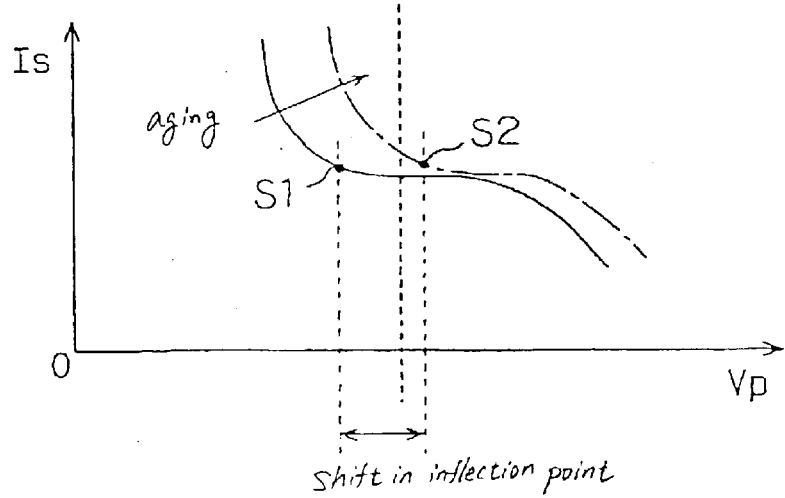
FIG. 18(b) shows a shift in current output of a sensor cell current airing from aging of a gas concentration sensor.
Figure 1:
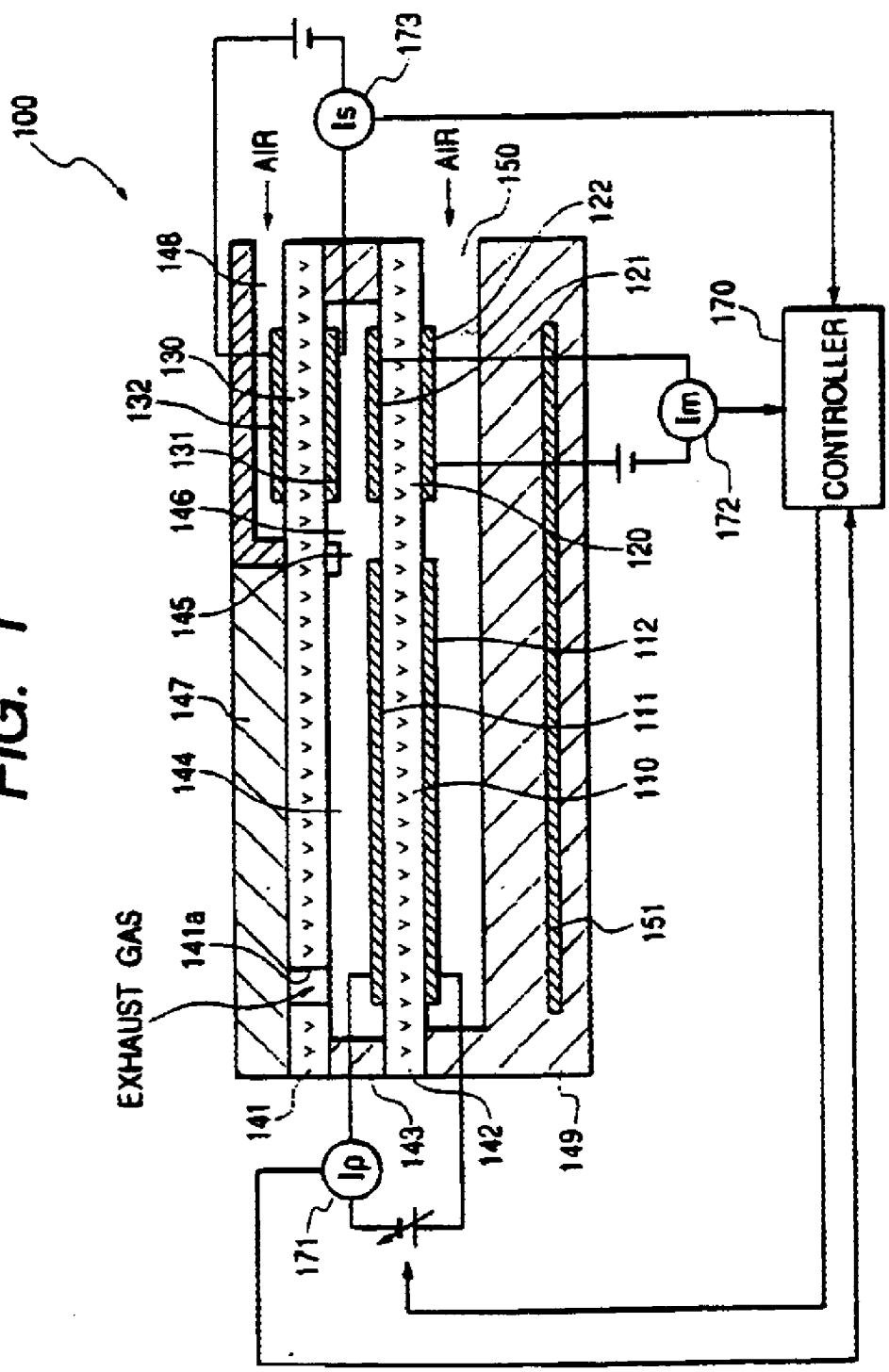
Figure 2A:
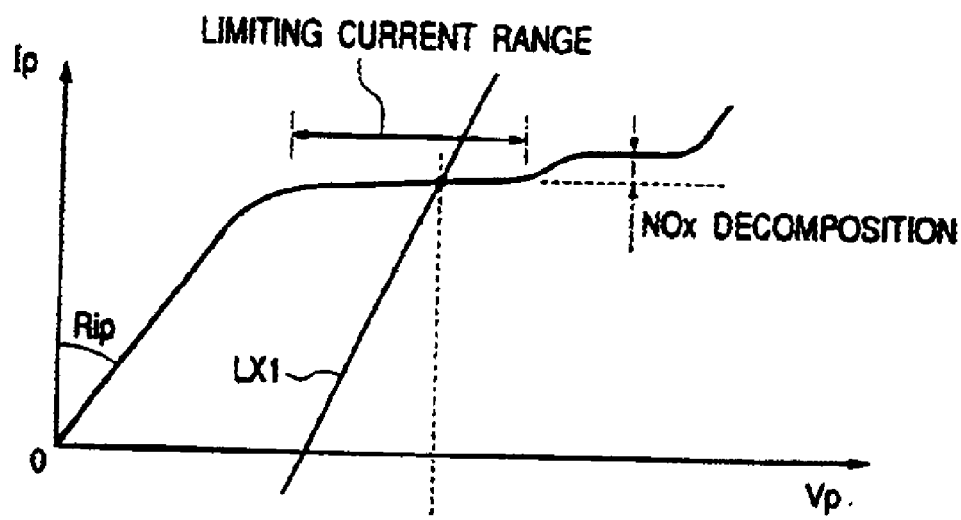
Figure 2B:
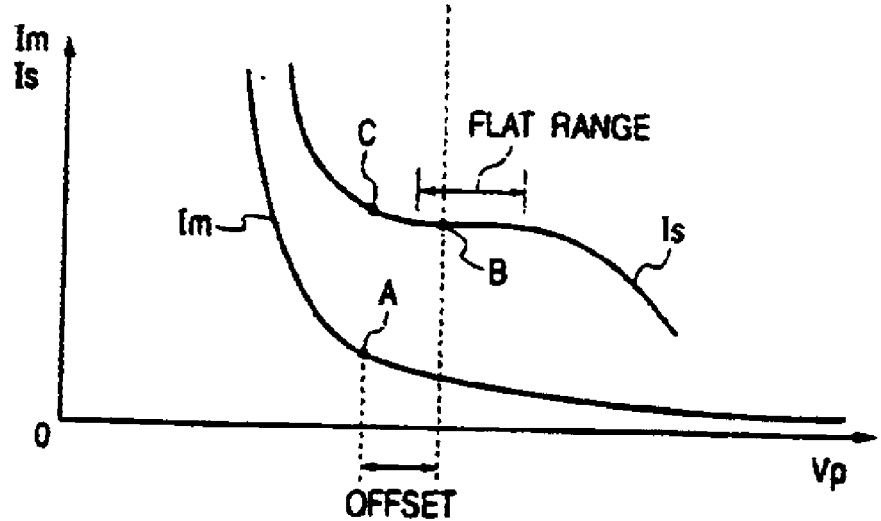
Figure 3A:
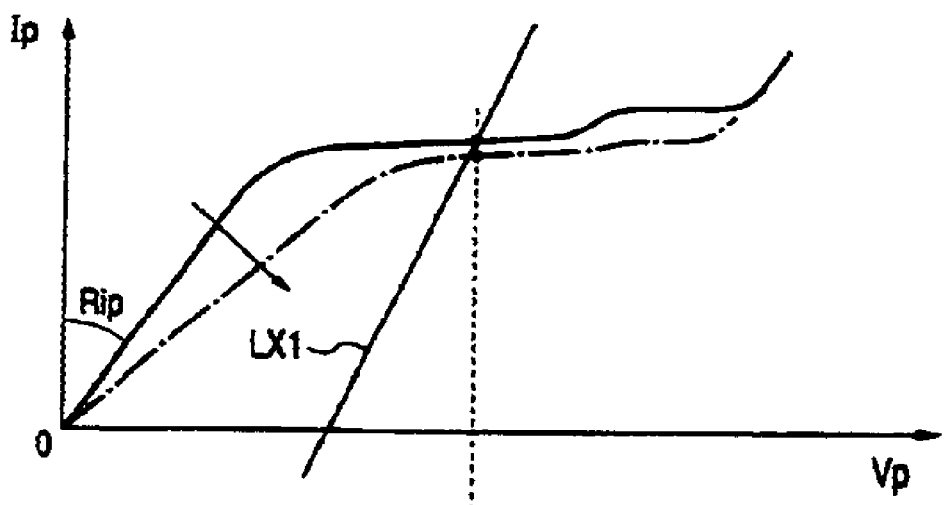
Figure 3B:
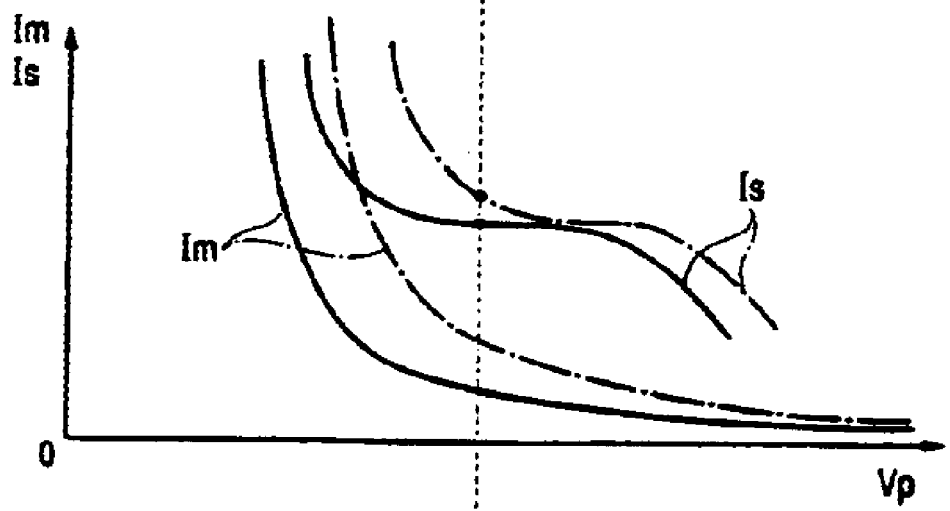
Figure 4A:
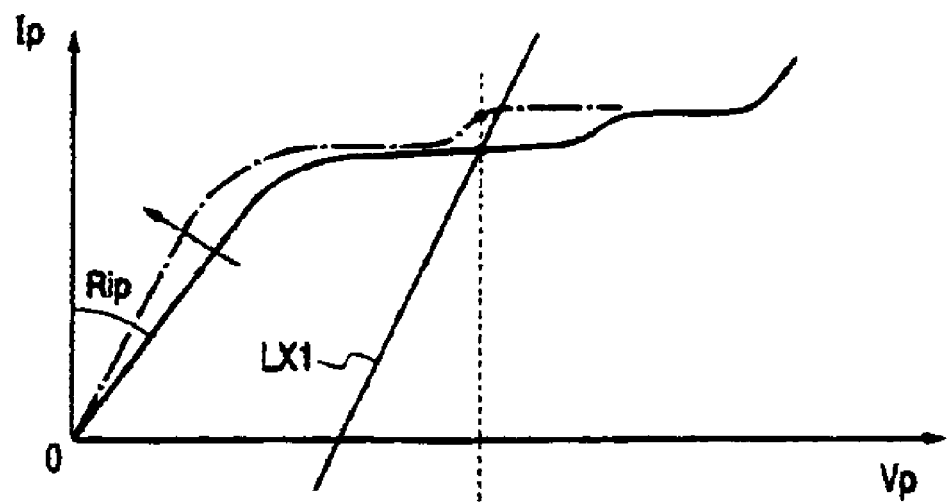
Figure 4B:
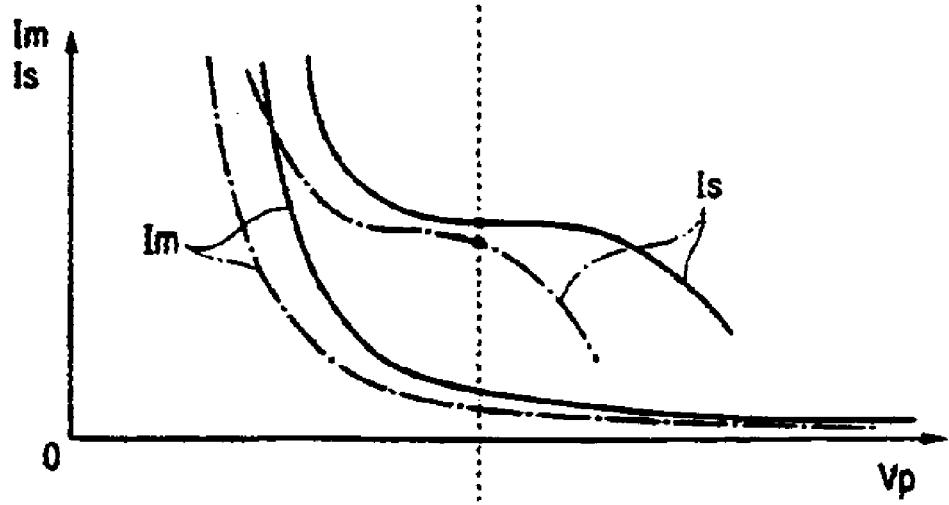
Figure 5:
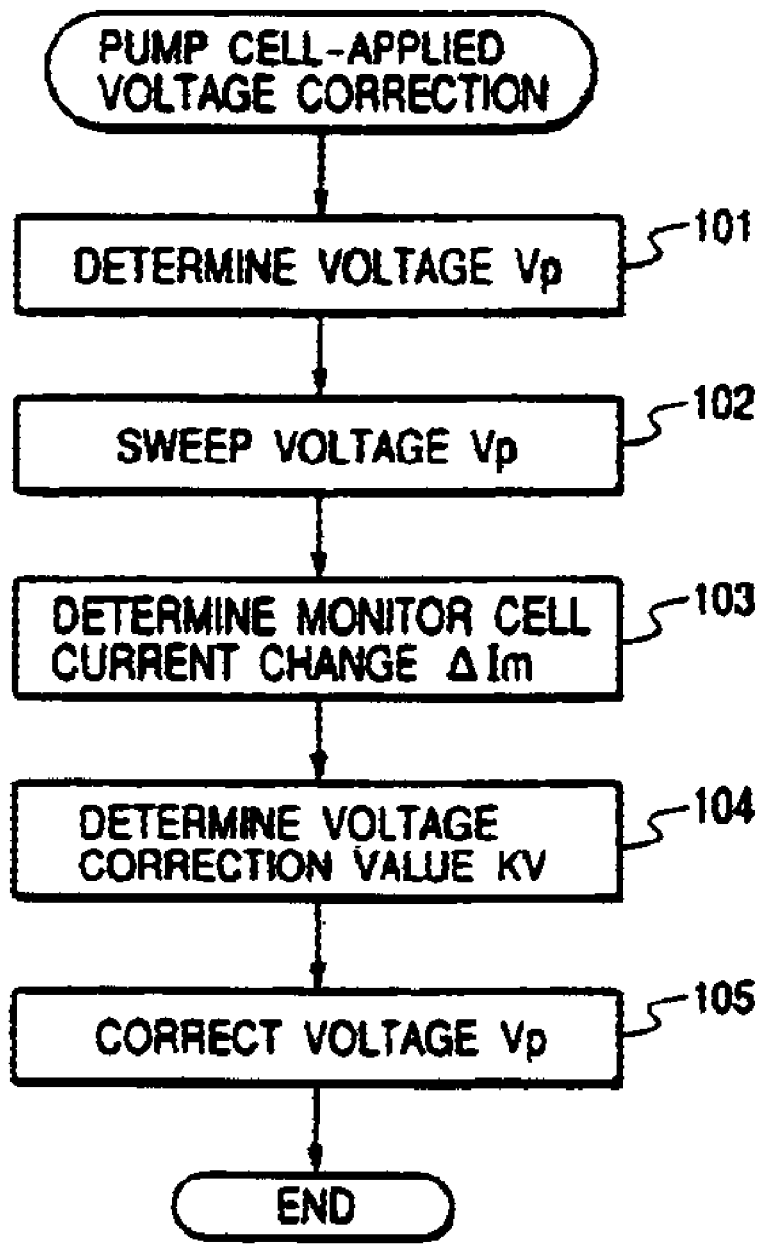
Figure 6:
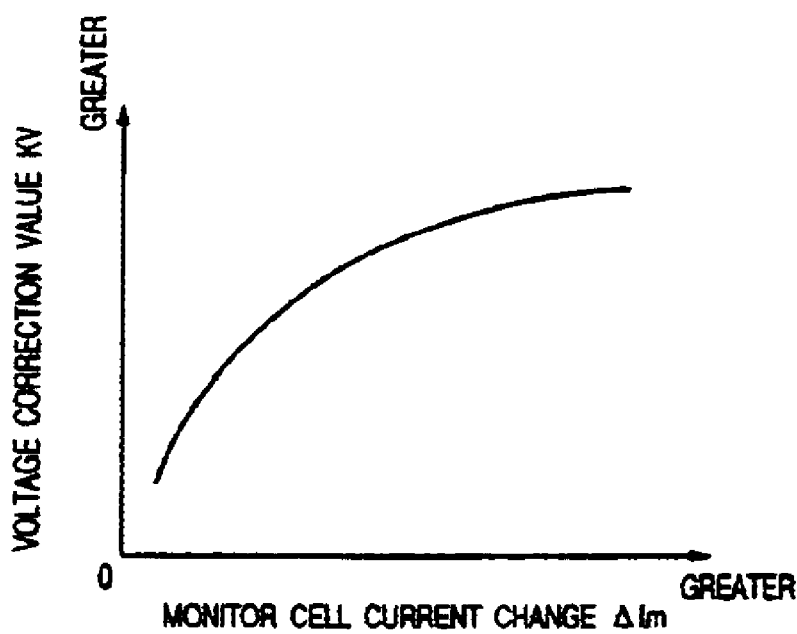
Figure 7:
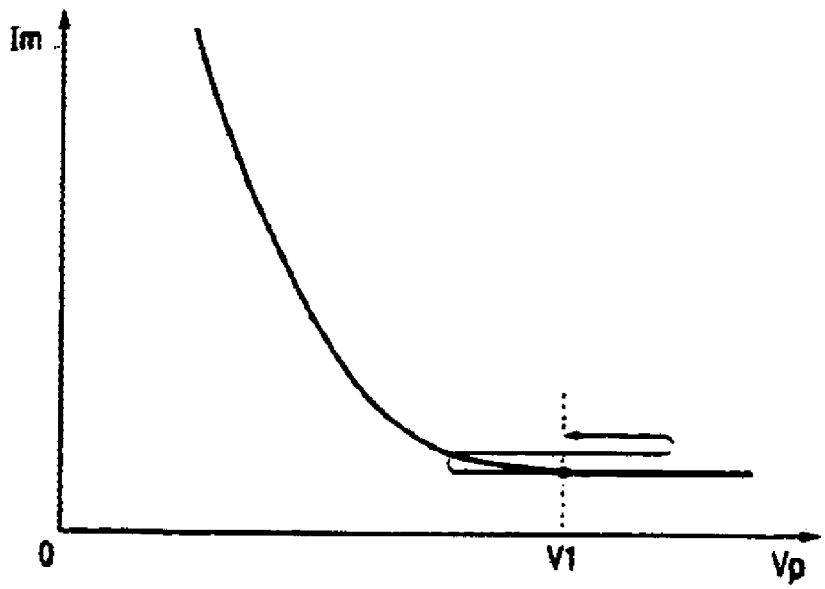
Figure 8A:
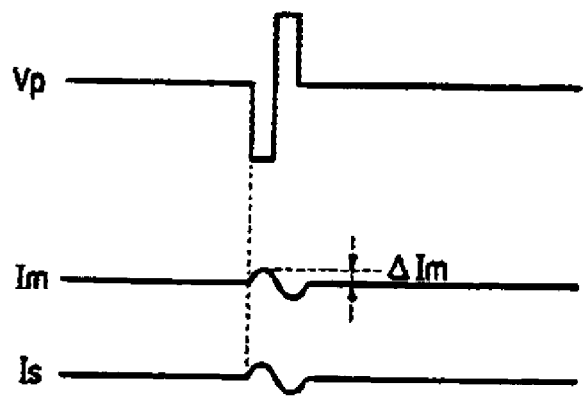
Figure 8B:
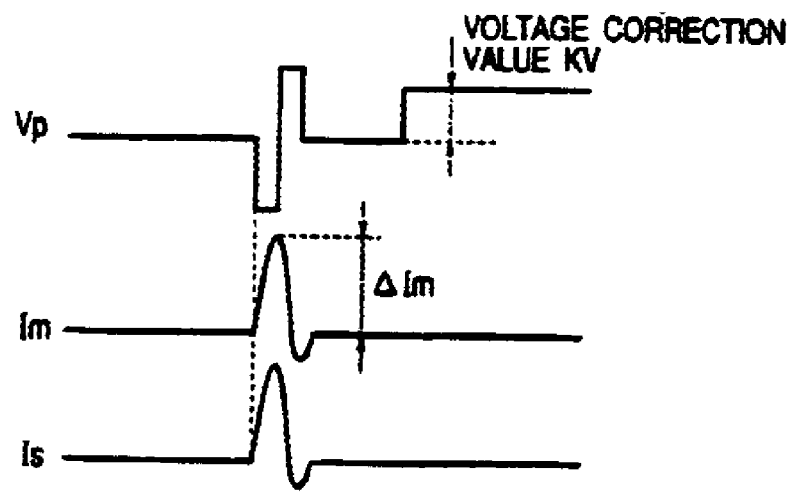
Figure 9:
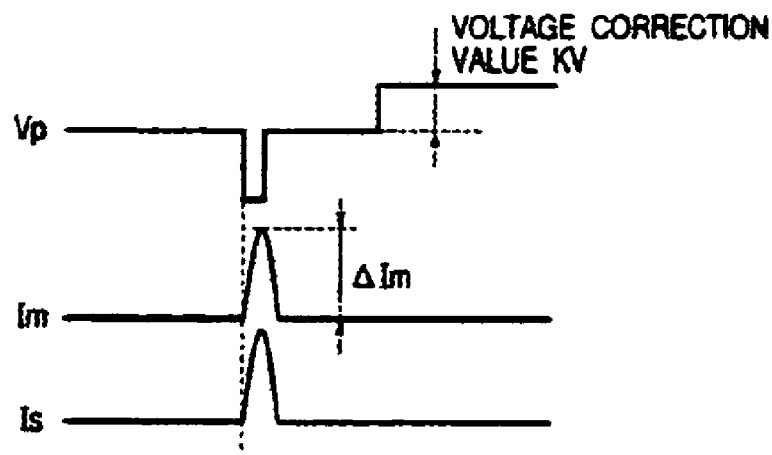
Figure 10:
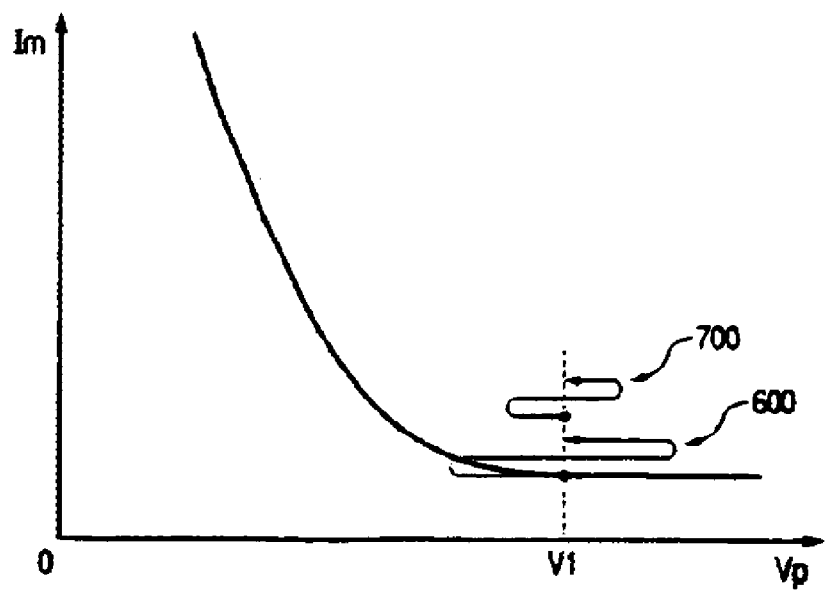
Figure 11:
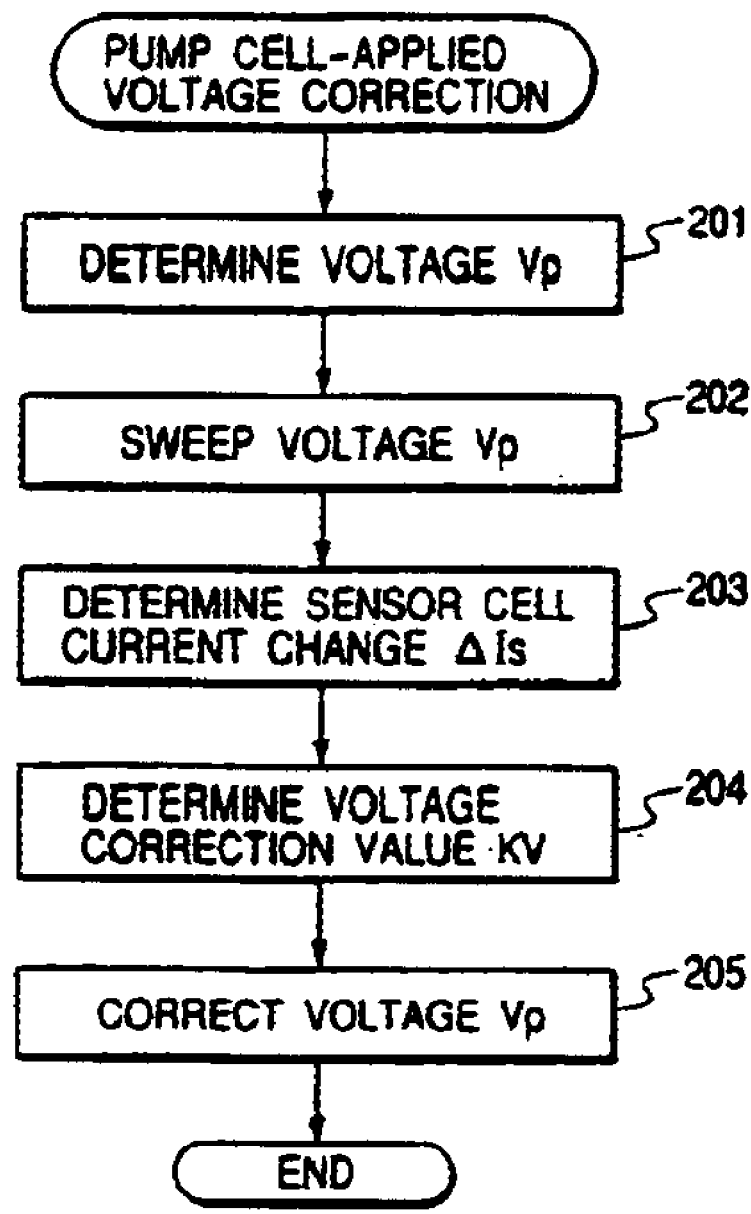
Figure 12:
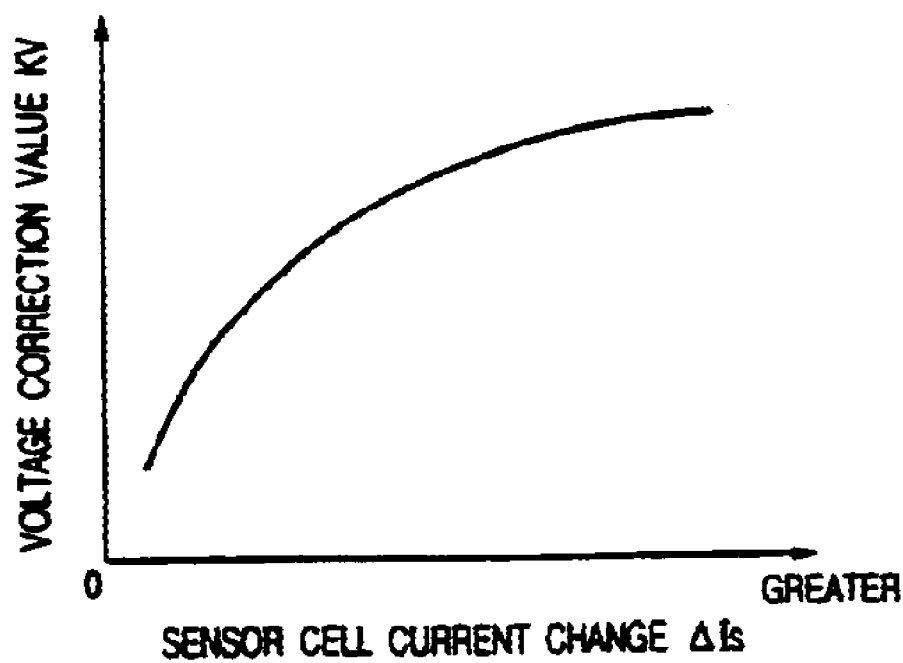
Figure 13A:
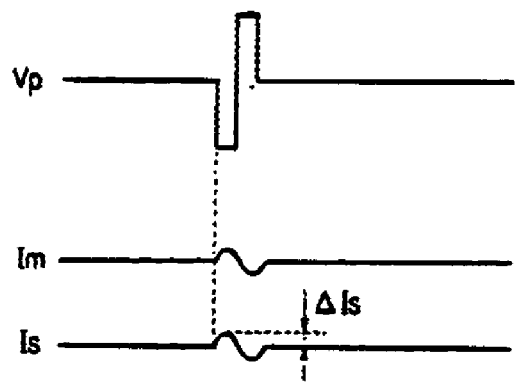
Figure 13B:
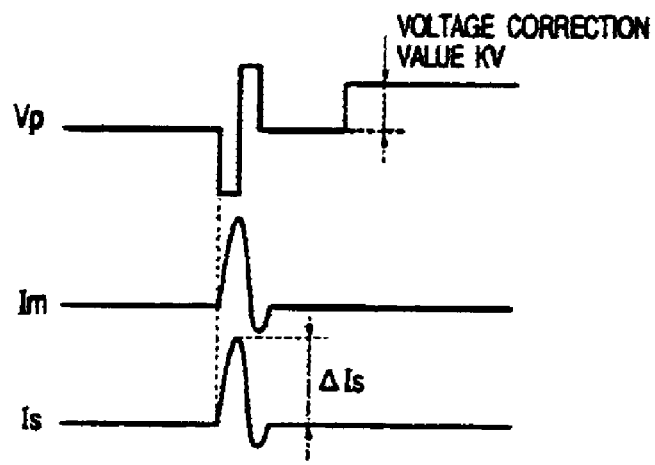
Figure 14:
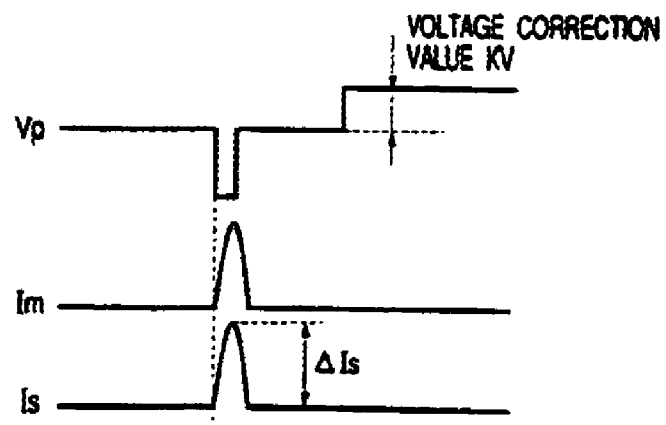
Figure 15:
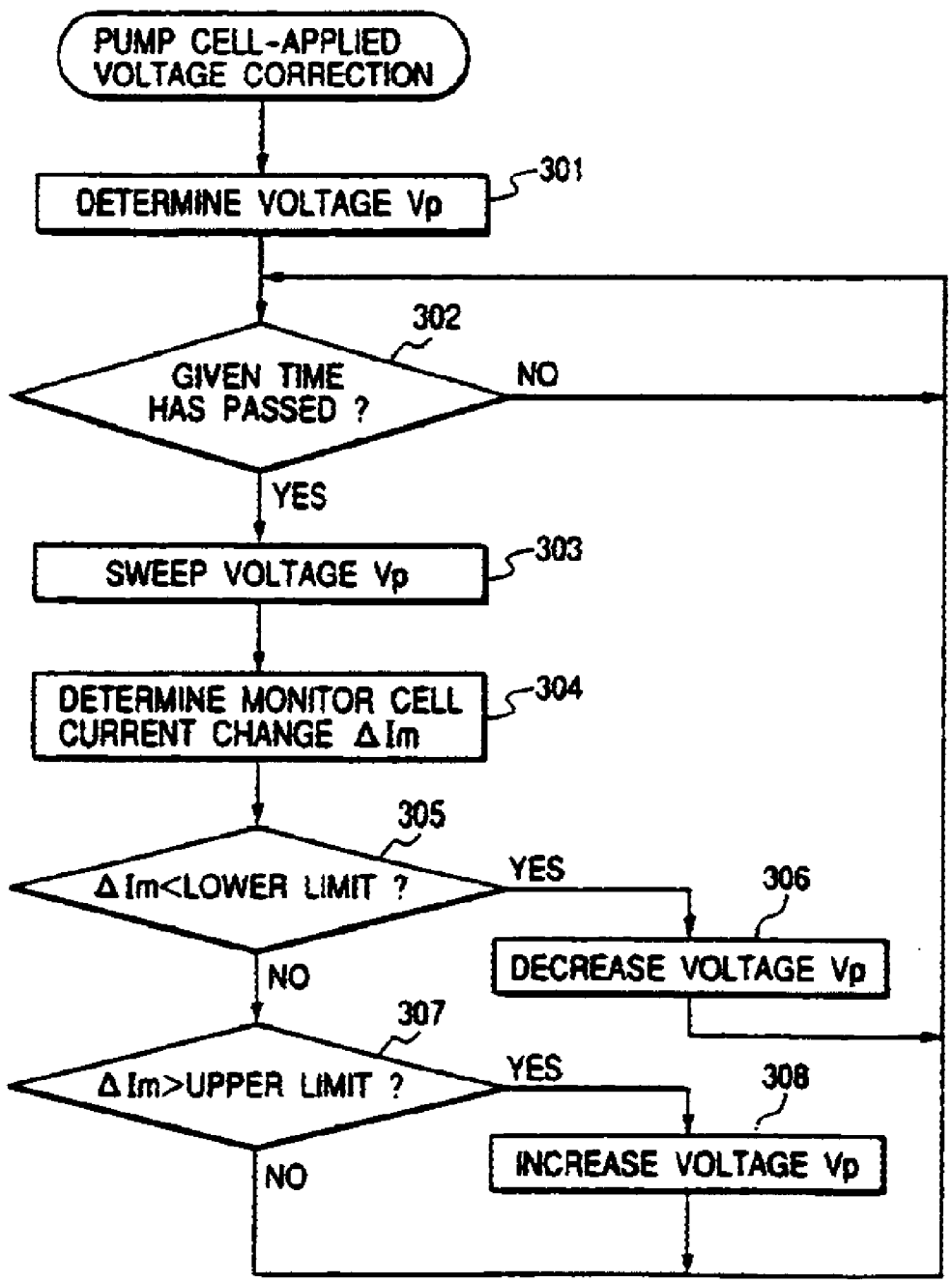
Figure 16C:
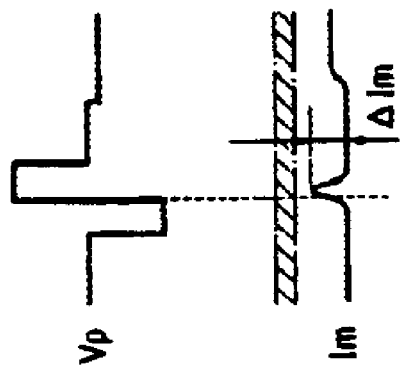
Figure 16B:
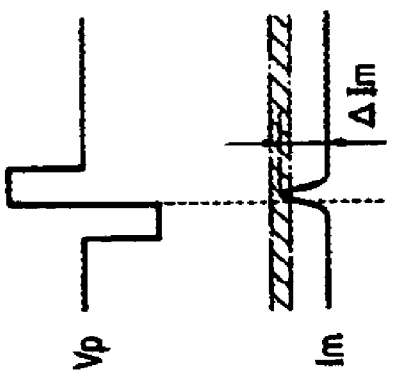
Figure 16A:
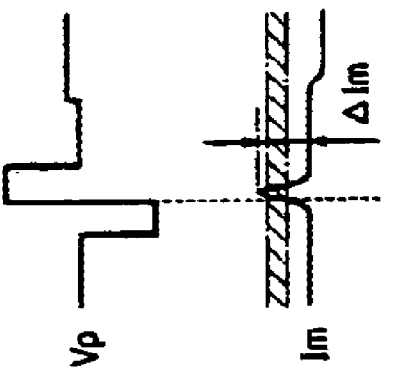
Figure 17A:
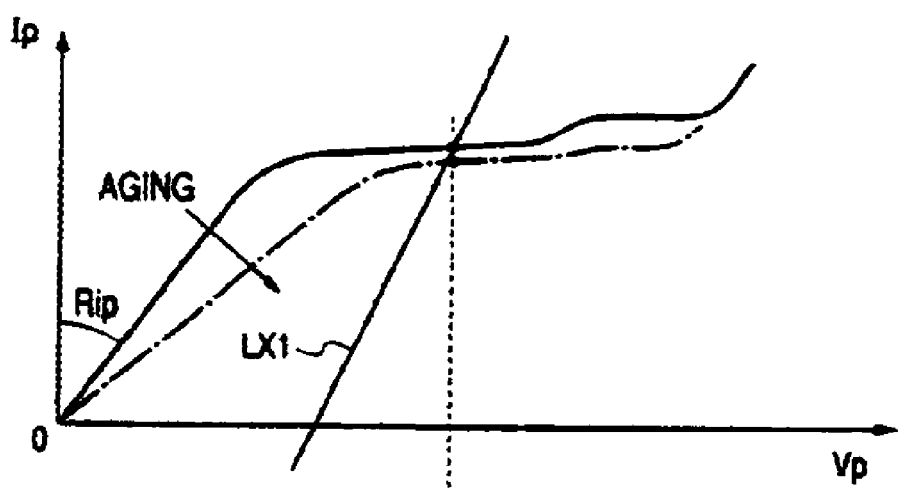
Figure 17B:
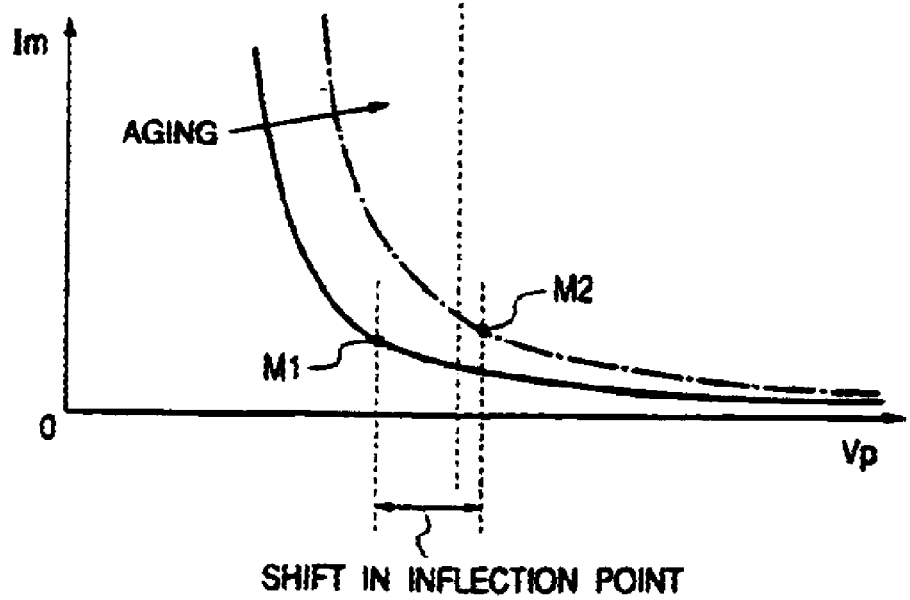
Figure 18A:
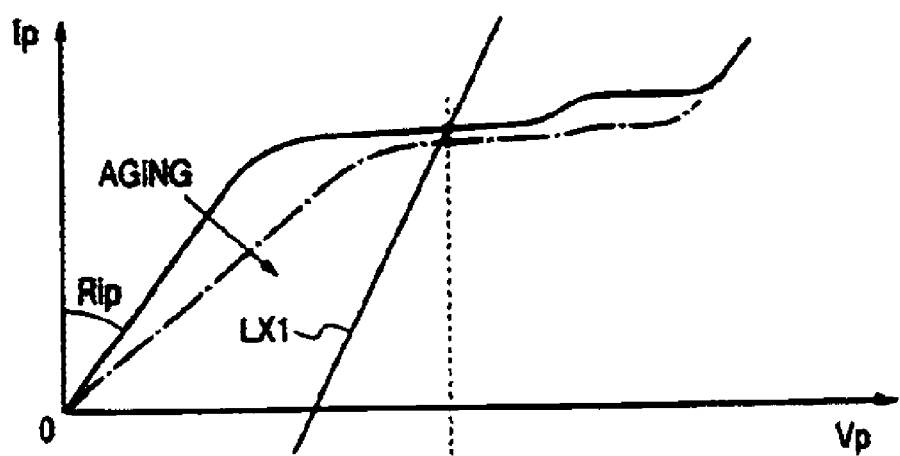
Figure 18B:
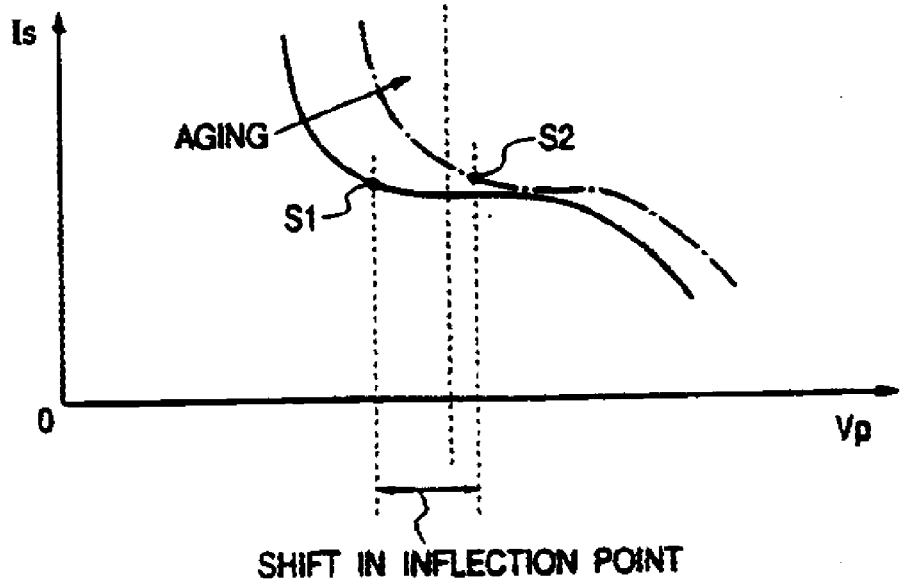

The degree of deterioration of the gas concentration sensor 100 may alternatively be determined using a shift in the inflection point of the sensor cell current Is instead of that of the monitor cell current Im. This is based on the fact that the inflection point of the sensor cell current Is is shifted, as shown in FIG. 18(b), to the higher level side of the pump cell-applied voltage Vp, from S1 to S2 as the deterioration of the gas concentration sensor 100 increases. The controller 170 sweeps the pump cell-applied voltage Vp temporarily to at least one of the positive and negative sides and uses a resulting value of the sensor cell current Is to determine the degree of deterioration of the gas concentration sensor 100.

The gas concentration measuring apparatus of this embodiment may be designed only to determine the deterioration of the gas concentration sensor 100 without functioning to correct the pump cell-applied voltage Vp using the monitor cell current Im and the sensor cell current Is.

In the above embodiments, an initial target value of the pump cell-applied voltage Vp is determined by look-up using the target applying voltage line LX1, but however, it may be fixed or determined stepwise as a function of the concentration of oxygen.

The correction of the pump cell-applied voltage Vp and/or the determination of the deterioration of the gas concentration sensor 100 may be made only at startup or rest of the engine. In this case, these operations are performed without measuring the concentration of gasses.

The gas concentration measuring apparatus in each of the above described embodiments may also be used with a multi-cell gas concentration sensor having more than three cells. For example, a gas concentration sensor equipped with two pump cells may be used.

A gas concentration sensor which is designed to decompose and discharge $O_2$ contained in gasses to be measured through a pump cell and decompose HC or CO contained in the gasses after the decomposition of $O_2$ through a sensor cell may be used in each of the above embodiments. Further, the gas concentration measuring apparatus in each of the above embodiments may also be used for measuring the concentration of gasses other than exhaust gasses of an automotive engine.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas concentration measuring apparatus comprising:
a gas concentration sensor including a gas chamber into which gasses are admitted, a pump cell responsive to application of a voltage to pump oxygen molecules contained in the gasses out of and into the gas chamber selectively and produce a pump cell current, a sensor cell working to produce a sensor cell current indicating a concentration of a specified gas component contained in the gasses having passed through the pump cell, and a monitor cell working to produce a monitor cell current indicative of a concentration of residual oxygen molecules within the gas chamber;
a pump cell-applied voltage determining circuit looking up a predetermined voltage-to-current relation to determine an initial value of the voltage to be applied to said pump cell as a function of the pump cell current produced by said pump cell; and
a pump cell-applied voltage correcting circuit working to apply the initial value of the voltage to the pump cell and sweep the initial value to at least one of higher and lower level sides, said pump cell-applied voltage correcting circuit correcting the initial value of the voltage applied to the pump cell as a function of a magnitude of the sensor cell current produced by the sensor cell upon a sweep of the initial value of the voltage applied to the pump cell.

2. A gas concentration measuring apparatus as set forth in claim 1, wherein said pump cell-applied voltage correcting circuit works to determine a difference between a value of the voltage applied to the pump cell appearing at an inflection point of a pump cell applied voltage-to-sensor cell current curve indicative of a relation between the voltage applied to the pump cell and a resulting value of the sensor cell current produced by the sensor cell and the initial value of the voltage applied to the pump cell based on the value of the sensor cell current produced upon the sweep of the voltage applied to the pump cell, the inflection point being defined by a level of the voltage applied to the pump cell at which a rate of a change in the sensor cell current changes over a given value, said pump cell-applied voltage correcting circuit correcting the initial value of the voltage applied to the pump cell based on the determined difference.

3. A gas concentration measuring apparatus as set forth in claim 1, wherein said pump cell-applied voltage correcting circuit sweeps the initial value of the voltage only to one of the higher and lower level sides, said pump cell-applied voltage correcting circuit correcting the initial value of the voltage applied to the pump cell as a function of the magnitude of the sensor cell current produced upon the sweep of the initial value of the voltage applied to the pump cell.

4. A gas concentration measuring apparatus as set forth in claim 1, wherein said pump cell-applied voltage correcting circuit sweeps the initial value of the voltage both to the higher and lower level sides, said pump cell-applied voltage correcting circuit correcting the initial value of the voltage applied to the pump cell as a function of the magnitude of the sensor cell current produced upon the sweep of the initial value of the voltage applied to the pump cell.

5. A gas concentration measuring apparatus as set forth in claim 1, wherein said pump cell-applied voltage correcting circuit sweeps the initial value of the voltage both to the higher and lower level sides sequentially to measure resulting changes in the sensor cell current, respectively, said pump cell-applied voltage correcting circuit comparing the changes with each other to determine whether the initial value of the voltage applied to the pump cell should be corrected or not as a function of a difference between the changes.

6. A gas concentration measuring apparatus as set forth in claim 1, wherein said pump cell-applied voltage correcting circuit sweeps the initial value of the voltage both to the higher and lower level sides sequentially to measure resulting changes in the sensor cell current, respectively, when the changes are different from those appearing initially at said gas concentration sensor and from each other, said pump cell-applied voltage correcting circuit shifting the initial value of the voltage applied to the pump cell to a direction opposite a direction in which the sensor cell current increases with a change in the voltage applied to the pump cell.

7. A gas concentration measuring apparatus as set forth in claim 1, wherein said pump cell-applied voltage correcting circuit determines a voltage correction value used in correcting the initial value of the voltage applied to the pump cell as a function of the sensor cell current upon the sweep of the initial value of the voltage applied to the pump cell and stores the voltage correction value in a backup memory.

8. A gas concentration measuring apparatus as set forth in claim 1, wherein said pump cell-applied voltage correcting circuit determines a voltage correction value as a function of the sensor cell current upon the sweep of the initial value of the voltage applied to the pump cell and corrects the predetermined voltage-to-current relation.

9. A gas concentration measuring apparatus as set forth in claim 1, wherein said pump cell-applied voltage correcting circuit controls the voltage applied to the pump cell so as to bring a value of the sensor cell current produced upon the sweep of the initial value of the voltage applied to the pump cell to within a given controlled range.

10. A gas concentration measuring apparatus as set forth in claim 9, wherein when the value of the sensor cell current produced upon the sweep of the initial value of the voltage applied to the pump cell lies outside of the given controlled range, said pump cell-applied voltage correcting circuit increases or decreases the voltage applied to the pump cell.

11. A gas concentration measuring apparatus as set forth in claim 1, wherein said pump cell-applied voltage correcting circuit sweeps the initial value of the voltage at different amplitudes sequentially to measure resulting changes in the sensor cell current and corrects the initial value of the voltage applied to the pump cell based on the changes in the sensor cell current.

12. A gas concentration measuring apparatus as set forth in claim 1, further comprising a deterioration determining circuit which works to determine a degree of deterioration of said gas concentration sensor based on the magnitude of the sensor cell current produced by the monitor cell upon the sweep of the initial value of the voltage applied to the pump cell.

13. A gas concentration measuring apparatus as set forth in claim 1, wherein said pump cell-applied voltage determining circuit determines the initial value of the voltage to be applied to said pump cell as a function of the pump cell current produced by said pump cell by look-up using the predetermined voltage-to-current relation for determining the concentration of the specified gas component in a gas concentration measuring cycle, and wherein said pump cell-applied voltage correcting circuit works to correct the initial value of the voltage applied to the pump cell in a correction cycle which does not coincide with the gas concentration measuring cycle.

14. A gas concentration measuring apparatus as set forth in claim 1, wherein when said pump cell-applied voltage correcting circuit sweeps the initial value of the voltage applied to the pump cell, resulting values of the monitor cell current and the sensor cell current are filtered to blur waveforms thereof.

15. A gas concentration measuring apparatus as set forth in claim 1, said gas concentration sensor works to measure the specified gas component contained in exhaust gasses of an automotive engines, and wherein said pump cell-applied voltage correcting circuit operates at at least one of startup and rest of the engine.

* * * * *

UNITED STATES PATENT AND TRADEMARK OFFICE
CERTIFICATE OF CORRECTION

PATENT NO. : 6,895,800 B2
DATED : May 24, 2005
INVENTOR(S) : Tomura et al.

It is certified that error appears in the above-identified patent and that said Letters Patent is hereby corrected as shown below:

Replace informal drawing Sheets 1-15 with formal attached drawings Sheets 1-15.

Signed and Sealed this

Fourteenth Day of February, 2006

JON W. DUDAS
*Director of the United States Patent and Trademark Office*

SHIFT IN INFLECTION POINT

SHIFT IN INFLECTION POINT